US008501694B2

(12) United States Patent
Lollar et al.

(10) Patent No.: US 8,501,694 B2
(45) Date of Patent: *Aug. 6, 2013

(54) METHOD OF ADMINISTERING PORCINE B-DOMAINLESS FVIII

(75) Inventors: John S. Lollar, Decatur, GA (US); Garrett E. Bergman, Narberth, PA (US)

(73) Assignees: Emory University, Atlanta, GA (US); Baxter International Inc., Deerfield, IL (US); Baxter Healthcare SA, Glattpark (Opfikon) (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/356,437

(22) Filed: Jan. 23, 2012

(65) Prior Publication Data
US 2012/0270788 A1 Oct. 25, 2012

Related U.S. Application Data

(60) Continuation of application No. 12/496,516, filed on Jul. 1, 2009, now Pat. No. 8,101,718, which is a division of application No. 11/549,049, filed on Oct. 12, 2006, now Pat. No. 7,576,181, which is a continuation-in-part of application No. PCT/US2005/014760, filed on Apr. 28, 2005.

(60) Provisional application No. 60/569,000, filed on May 7, 2004, provisional application No. 60/568,015, filed on May 3, 2004.

(51) Int. Cl.
*A61K 38/37* (2006.01)
*A61P 7/04* (2006.01)

(52) U.S. Cl.
USPC .......................... 514/14.1; 530/383

(58) Field of Classification Search
USPC .......................... 514/14.1; 530/383
See application file for complete search history.

(56) References Cited

U.S. PATENT DOCUMENTS

| 4,348,384 | A | 9/1982 | Horikoshi et al. |
| 4,757,006 | A | 7/1988 | Toole |
| 4,868,112 | A | 9/1989 | Toole |
| 5,364,771 | A | 11/1994 | Lollar |
| 5,563,045 | A | 10/1996 | Pittman et al. |
| 5,565,427 | A | 10/1996 | Freudenberg |
| 5,583,209 | A | 12/1996 | Lollar et al. |
| 5,605,884 | A | 2/1997 | Lee et al. |
| 5,663,060 | A | 9/1997 | Lollar et al. |
| 5,733,873 | A | 3/1998 | Osterberg et al. |
| 5,744,446 | A | 4/1998 | Lollar et al. |
| 5,763,401 | A | 6/1998 | Nayar |
| 5,859,204 | A | 1/1999 | Lollar |
| 5,874,408 | A | 2/1999 | Nayar |
| 5,888,974 | A | 3/1999 | Lollar et al. |
| 5,925,739 | A | 7/1999 | Spira et al. |
| 5,935,935 | A | 8/1999 | Connelly et al. |
| 5,962,650 | A | 10/1999 | Osterberg et al. |
| 5,972,885 | A | 10/1999 | Spira et al. |
| 6,180,371 | B1 | 1/2001 | Lollar |
| 6,200,560 | B1 | 3/2001 | Couto et al. |
| 6,376,463 | B1 | 4/2002 | Lollar |
| 6,458,563 | B1 | 10/2002 | Lollar |
| 6,642,028 | B1 | 11/2003 | Ill et al. |
| 6,759,216 | B1 | 7/2004 | Lollar |
| 6,770,744 | B2 | 8/2004 | Lollar |
| 6,818,439 | B1 | 11/2004 | Jolly et al. |
| 7,012,132 | B2 | 3/2006 | Lollar |
| 7,033,791 | B2 | 4/2006 | Lollar |
| 7,122,634 | B2 | 10/2006 | Lollar |
| 7,560,107 | B2 | 7/2009 | Lollar |
| 7,576,181 | B2 | 8/2009 | Lollar et al. |
| 8,101,718 | B2 | 1/2012 | Lollar et al. |
| 2004/0249134 | A1 | 12/2004 | Lollar |
| 2005/0009148 | A1 | 1/2005 | Lollar |
| 2005/0118684 | A1 | 6/2005 | Lollar |
| 2005/0123997 | A1 | 6/2005 | Lollar |
| 2007/0135342 | A1 | 6/2007 | Lollar |
| 2007/0173446 | A1 | 7/2007 | Lollar |
| 2009/0325881 | A1 | 12/2009 | Lollar |

FOREIGN PATENT DOCUMENTS

| EP | 0182448 | 5/1986 |
| EP | 0306968 | 3/1989 |
| WO | 89/09784 | 10/1989 |
| WO | 91/07438 | 5/1991 |

(Continued)

OTHER PUBLICATIONS

Patent prosecution for parent patent 7,576,181, filed Oct. 12, 2006, issued Aug. 18, 2009, (downloaded May 15, 2012), last document dated Apr. 13, 2009, 52 pp.
Prosecution history for parent patent 8,101,718, filed Jul. 1, 2009, issued Jan. 24, 2012, (downloaded May 15, 2012), last document dated Sep. 20, 2011, 53 pp.
Prosecution history for U.S. Patent 6,458,563 with related subject matter and inventor in common, filed Mar. 10, 2000, issued Oct. 1, 2002, 25 pp.
Prosecution history for related U.S. Appl. No. 12/491,734, filed Jun. 25, 2009 (downloaded May 15, 2012), last document dated Apr. 6, 2012, 40 pp.
Patent disclosure of related U.S. Appl. No. 13/431,085, filed Mar. 27, 2012, 87 pp.
Supplementary European Search Report, corresponding to EP 01910853, application with related technology and inventor in common, completed Sep. 10, 2004, 3 pages.

(Continued)

*Primary Examiner* — Chih-Min Kam
(74) *Attorney, Agent, or Firm* — Lathrop & Gage LLP

(57) ABSTRACT

The present invention provides a method of administering porcine B-domainless factor VIII (OBI-1) to a patient having factor VIII deficiency to provide more rapid and effective protection against bleeding episodes, compared to formerly available methods, or to provide more effective protection to such patients during non-bleeding periods. This invention is based on the discovery that the recombinant B-domainless porcine fVIII, termed OBI-1, has greater bioavailability compared to the natural porcine fVIII partially purified from porcine plasma, termed HYATE:C. Therefore, the inventive method employs lower unit doses of OBI-1, including, alternatively, omission of antibody-neutralizing dosage, or has longer intervals between the administration, compared to HYATE:C, to provide equivalent protection in patients having fVIII deficiency. The invention further provides pharmaceutical compositions and kits containing OBI-1 in combination with a pharmaceutically acceptable carrier, that are useful for treating patients in need of fVIII more effectively.

4 Claims, 4 Drawing Sheets

FOREIGN PATENT DOCUMENTS

| WO | 93/20093 | 10/1993 |
|---|---|---|
| WO | 94/07510 | 4/1994 |
| WO | 94/11503 | 5/1994 |
| WO | 95/24427 | 9/1995 |
| WO | 97/03191 | 1/1997 |
| WO | 97/03193 | 1/1997 |
| WO | 99/46274 | 9/1999 |
| WO | 00/71141 | 11/2000 |
| WO | 01/68109 | 9/2001 |
| WO | 03/080108 | 10/2003 |
| WO | 2005/107776 | 11/2005 |

OTHER PUBLICATIONS

International Preliminary Examination Report and Search Report, corresponding to PCT/US01/05076, application with related technology and inventor in common, mailed Mar. 3, 2003 and Jun. 22, 2001, 7 pages.

International Preliminary Examination Report, Written Opinion, and Search Report, corresponding to PCT/US05/14760, priority application with related technology and inventor in common, mailed Nov. 16, 2006 and Oct. 4, 2005, 9 pages.

Supplementary European Search Report, corresponding to EP 05740319.8, application with related technology and inventor in common, mailed May 15, 2009, 3 pages.

European Office Action, corresponding to EP 05740319.8, application with related technology and inventor in common, mailed Aug. 6, 2009, 4 pages.

European Office Action response in EP 05740319.8, application with related technology and inventor in common, dated Apr. 15, 2010, 3 pp.

European Second Office Action, dated Mar. 8, 2011, in EP 05740319.8, application with related technology and inventor in common, 4 pp.

European Second Office Action response in EP 05740319.8, application with related technology and inventor in common, dated Dec. 22, 2011, 8 pp.

European Third Office Action, dated Mar. 21, 2012, in EP 05740319.8, application with related technology and inventor in common, 4 pp.

Translation of First Japanese Office Action in JP 2007-511442, application with related technology and inventor in common, mailed Jun. 1, 2010, 6 pages.

Japanese associate correspondence regarding response to First Office Action in JP 2007-511442, application with related technology and inventor in common, dated Nov. 30, 2010, 3 pp.

Translation of Second Japanese Office Action in JP 2007-511442, application with related technology and inventor in common, mailed Mar. 22, 2011, 6 pages.

Japanese associate correspondence regarding Second Office Action in JP 2007-511442, application with related technology and inventor in common, dated Sep. 22, 2011, 9 pp.

Translation of Third Japanese Office Action in JP 2007-511442, application with related technology and inventor in common, mailed Feb. 14, 2012, 3 pages.

Product Insert, "Antihemophilic Factor, [Porcine]-Hyate:C®," 2000 (Oct. 2000 revision date); Ipsen, Inc., Milford, MA, 4 pp.

"Antihemophilic Factor (Systemic)" (Revised Jul. 8, 2001) Hyate: C Professional Drug Information from URL http://www.drugs.com/mmx/hyate-c.html, 17 pp. (downloaded Dec. 28, 2007).

Barrow et al. (Jan. 15, 2000) "Reduction of the Antigenicity of Factor VIII Toward Complex Inhibitory Antibody Plasmas Using Multiply-Substituted Hybrid Human/Porcine Factor VIII Molecules," Blood 95(2):564-568.

Barrow et al. (2001) "Antigenicity of Putative Phospholipid Membrane-Binding Residues in Factor VIII," Blood 97(1):169-174.

Barrow et al. (Aug. 2006) "Neutralization of Antifactor VIII Inhibitors by Recombinant Porcine Factor VIII," J. Thromb. Haemost. 4:2223-2229.

Barrowcliffe et al (2002) "Coagulation and Chromogenic Assays of Factor VIII Activity: General Aspects, Standardization, and Recommendations," Semin. Thromb. Hemost. 28:247-256.

Bergman et al. (2004) "Comparative Immunogenicity of Two Forms of Porcine Factor VIII in Cynomolgus Monkeys," Blood (ASH Annual Meeting Abstracts). 104:841A, Abstract No. 3079.

Bihoreau et al. (1991) "Structural and Functional Characterization of VIII-Delta. A New Recombinant Factor VIII Lacking Most of the B-Domain," Biochem. J. 277:23-31.

Bithell, T.C. (1993) "The Diagnostic Approach to the Bleeding Disorders," Chapter 48 in Lee GR, Bithell TC, Foerster J, Athens JW and Lukens JN [eds], Wintrobe's Clinical Hematology, ninth edition, Lea & Febiger, Malvern, PA, pp. 1301-1324.

Chang et al. (1998) "Changing Residue 338 in Human Factor IX from Arginine to Alanine Causes an Increase in Catalytic Activity," J. Biol. Chem. 273(20):12089-12094.

Church et al. (1984) "Coagulation Factors V and VIII and Ceruloplasmin Constitute a Family of Structurally Related Proteins," Proc. Nat. Acad. Sci. USA 81:6934-6937.

Doehring et al. (2002) "High Level Expression of Recombinant Porcine Coagulation Factor VIII," J. Biol. Chem. 277(41):38345-38349.

Dominguez et al. (1994) "Gene Walking by Unpredictable Primed PCR," Nuc. Acids Res. 22(15):3247-3248.

Eaton et al. (1986) "Construction and Characterization of an Active Factor VIII Variant Lacking the Central One-Third of the Molecule," Biochem. 25(26):8343-8347.

Ewenstein et al. (Feb. 2002) "Pharmacokinetic Analysis of Plasma-Derived and Recombinant F IX Concentrates in Previously Treated Patients with Moderate or Severe Hemophilia B," Transfusion 42(2):190-197.

Fulcher et al. (1985) "Localization of Human Factor FVIII Inhibitor Epitopes to Two Polypeptide Fragments," Proc. Nat. Acad. Sci. USA 82:7728-7732.

Gatti et al. (1984) "Use of Porcine Factor VIII in the Management of Seventeen Patients with Factor VIII Antibodies," Throm. Haemost. 51:379-384.

Gitschier et al. (1984) "Characterization of the Human Factor VIII Gene," Nature 312:326-330.

Hay et al. (1995) "Porcine Factor VIII Therapy in Patients with Factor VIII Inhibitors," Inhibitors to Coagulation Factors [L.M. Aledort et al. eds.] Plenum Press, New York, pp. 143-151.

Hay, C.R.M. (2000) "Porcine Factor VIII: Past, Present and Future," Haematologica 85:21-25.

Healy et al. (1996) "The cDNA and Derived Amino Acid Sequence of Porcine Factor VIII," Blood 88:4209-4214.

Kasper et al. (1975) "A More Uniform Measurement of Factor VIII Inhibitors," Thromb. Diath. Haemorrh. 34:869-872.

Kernoff, P.B.A. (1984) "Porcine Factor VIII: Preparation and Use in Treatment of Inhibitor Patients," Factor VIII Inhibitors [L.W. Hoyer, ed.] Alan R. Liss, New York, pp. 207-224.

Kessler et al. (2005) "B-Domain Deleted Recombinant Factor VIII Preparations are Bioequivalent to a Monoclonal Antibody Purified Plasma-Derived Factor VIII Concentrate: A Randomized, Three-Way Crossover Study," Hemophilia 11:84-91.

Lind et al. (1995) "Novel Forms of B-Domain-Deleted Recombinant Factor VIII Molecules: Construction and Biochemical Characterization," Eur. J. Biochem. 232:19-27.

Lollar et al. (1991) "Structural Basis for the Decreased Procoagulant Activity of Human Factor VIII Compared to the Porcine Homolog," J. Biological Chem. 266:12481-12486.

Lollar et al. (1992) "Coagulant Properties of Hybrid Human/Porcine Factor VIII Molecules," J. Biological Chem. 267(33):23652-23657.

Lollar, P. (2000) "Mapping Factor VIII Inhibitor Epitopes Using Hybrid Human/Porcine Factor VIII Molecules," Haematologica 85(10s):26-30.

Lubin et al. (1994) "Elimination of a Major Inhibitor Epitope in Factor VIII," J. Biol. Chem. 269:8639-8641.

Mahlangu et al. (Nov. 2007) "A Phase II Open-Label Study Evaluating Hemostatic Activity, Pharmacokinetics and Safety of Recombinant Porcine Factor VIII (OBI-1) in Hemophilia A Patients with Alloantibody Inhibitors Directed Against Human FVIII" Blood (ASH Annual Meeting Abstracts), 110:241A, Abstract No. 783.

Martinowitz et al. (1992) "Adjusted Dose Continuous Infusion of Factor VIII in Patients with Haemophilia A", British Journal of Haematology 82:729-734.

Meulien et al. (1988) "A New Recombinant Procoagulant Protein Derived from the cDNA Encoding Human Factor VIII," Prot. Eng. 2:301-306.

Morfini et al. (2003) "A multicenter pharmacokinetic study of the B-domain deleted recombinant factor VIII concentrate using different assays and standards," Journal of Thrombosis and Haemostasis 1:2283-2289.

Morrison et al. (1993) "Use of Porcine Factor VIII in the Treatment of Patients with Acquired Hemophilia," Blood 81:1513-1520.

Nakai et al. (1994) "Properties of Affinity Purified Anti-Factor VIII Antibodies from Patients with Factor VIII Inhibitors," Coagulation-I 59a:224, 1p.

Ochman et al. (1990) "Inverse Polymerase Chain Reaction," Biotechnology 8:759-760.

Parker et al. (1991) "Targeted Gene-Walking Polymerase Chain Reaction," Nuc. Acids Res. 19(11):3055-3060.

Parker et al. (1991) "The Oligomer Extension 'Hot Blot'; A Rapid Alternative to Southern Blots for Analyzing Polymerase Chain Reaction Products," Biotechniques 10(1):94-101.

Parker et al. (2003) "Comparative Immunogenicity of Recombinant B Domain-Deleted Porcine Factor VIII and Hyate:C in Hemophilia A Mice Pre-Sensitized to Human Factor VIII," Blood 102(11):798a, Abstract #2956.

Parker et al. (2004) "Comparative Immunogenicity of Recombinant B Domain-Deleted Porcine Factor VIII and Hyate:C in Hemophilia A Mice Presensitized to Human Factor VIII," J. Thrombosis and Haemosiasis. 2:605-611.

Pittman et al. (1993) "Biochemical, Immunological and In Vivo Functional Characterization of B-Domain-Deleted Factor VIII," Blood 81(11):2925-2935.

Prescott et al. (1997) "The Inhibitor Antibody Response is More Complex in Hemophilia A Patients Than in Most Nonhemophiliacs with Factor VIII Autoantibodies," Blood 89(10):3663-3671.

Rickard, K.A. (1995) "Guidelines for therapy and optimal dosages of coagulation factors for treatment of bleeding and surgery in haemophilia," Haemophilia 1(Suppl 1):8-13.

Roberts et al. (2001) "Hemophilia A and Hemophilia B," Chapter 123 in Beutler E, Lichtman M, Coller B, Kipps T and Seligsohn U [Eds], Williams Hematology, 6th edition, pp. 1639-1657, McGraw-Hill, New York.

Sarker et al. (1993) "Restriction-Site PCR: A Direct Method of Unknown Sequence Retrieval Adjacent to a Known Locus by Using Universal Primers," PCR Meth. Appl. 2:318-322.

Sarver et al. (1987) "Stable Expression of Recombinant Factor VIII Molecule Using a Bovine Papillomavirus Vector," DNA 6(6):553-564.

Scandella et al. (1988) "Epitope Mapping of Human Factor VIII Inhibitor Antibodies by Deletion Analysis of Actor VIII Fragments Expressed in *Escherichia coli*," Proc. Nat. Acad. Sci. USA 85:6152-6156.

Scandella et al. (1989) "Localization of Epitopes for Human Factor VIII Inhibitor Antibodies by Immunoblotting and Antibody Neutralization," Blood 74(5):1618-1626.

Scandella et al. (1993) "A Recombinant Factor VIII A2 Domain Polypeptide Quantitatively Neutralizes Human Inhibitor Antibodies that Bind to A2," Blood 82(6):1767-1775.

Scandella et al. (1995) "Some Factor VIII Inhibitor Antibodies Recognize a Common Epitope Corresponding to C2 Domain Amino Acids 2248 Through 2312, Which Overlap a Phospholipid-Binding Site," Blood 86(5):1811-1819.

Siebert et al. (1995) "An Improved PCR Method for Walking in Uncloned Genomic DNA," Nuc. Acids Res. 23(6):1087-1088.

Srivastava et al. (1998) "Low-Dose Intermittent Factor Replacement for Post-Operative Haemostasis in Haemophilia," Haemophilia 4:799-801.

Toole et al. (1984) "Molecular Cloning of a cDNA Encoding Human Antihaemophilic Factor," Nature 312:342-347.

Toole et al. (1986) "A Large Region (≈90 kDa) of Human Factor VIII is Dispensable for In Vitro Procoagulant Activity," Proc. Nat. Acad. Sci. USA 83:5939-5942.

Vehar et al. (1984) "Structure of Human Factor VIII," Nature 312:337-342.

Verma et al. (Sep. 1997) "Gene Therapy—Promises, Problems and Prospects," Nature 389:239-242.

Zhong et al. (1998) "Some Human Inhibitor Antibodies Interfere with Factor VIII Binding to Factor IX," Blood 92(1):136-142.

European Third Office Action response, dated Oct. 1, 2012, in EP 05740319.8, application with related technology and inventor in common, 4 pp.

European Fourth Office Action, dated Oct. 10, 2012, in EP 05740319.8, application with related technology and inventor in common, 4 pp.

European Fourth Office Action response, dated Feb. 5, 2013, in EP 05740319.8, application with related technology and inventor in common, 4 pp.

METHOD OF ADMINISTERING PORCINE B-DOMAINLESS FVIII

CROSS-REFERENCE TO RELATED APPLICATIONS

This application is a continuation of U.S. patent application Ser. No. 12/496,516, filed Jul. 1, 2009, issued as U.S. Pat. No. 8,101,718 on Jan. 24, 2012, which application is a division of U.S. patent application Ser. No. 11/549,049, Oct. 12, 2006, issued as U.S. Pat. No. 7,576,181 on Aug. 18, 2009, which is a continuation-in-part of PCT/US2005/014,760 filed Apr. 28, 2005, which claims benefit of U.S. Provisional Application No. 60/568,015 filed May 3, 2004 and U.S. Provisional Application No. 60/569,000 filed May 7, 2004, all of which are incorporated herein to the extent not inconsistent herewith.

BACKGROUND OF THE INVENTION

Hemophilia A is a disease characterized by a defect in blood clotting which results in a variety of clinical symptoms and is ultimately life-threatening. Standard treatment of the disease is administration of clotting factor VIII (fVIII), a 300 kDa plasma protein missing or deficient in Hemophilia A patients. The therapy does not cure the underlying disease, but it ameliorates the symptoms. Therefore, patients must receive repeated doses of fVIII over their lifetimes. Although the administration of human fVIII to hemophilia A patients is an effective treatment, long-term therapy results in reduced efficacy for a significant proportion of the patient population. About 20-35% of hemophilia A patients develop inhibitory antibodies to human fVIII, regardless of whether the human fVIII is plasma-derived or made by recombinant technology. Patients who develop inhibitory antibodies to human fVIII experience reduced efficacy of treatment and longer bleeding episodes. Such patients have been successfully treated with porcine fVIII, which is a substantially homologous protein. Porcine fVIII is often significantly less reactive to the anti-human fVIII antibodies found in inhibitor patients. HYATE:C, a natural porcine fVIII partially purified from pooled porcine plasma, had long been commercially available. Both human and porcine fVIII purified from plasma pose potential hazards of contamination from virus or prion particles. Such hazards are of special concern for hemophiliacs, who will receive repeated doses over a lifetime of therapy. Recombinant human fVIII, and, more recently, recombinant porcine fVIII, have been developed for their respective indications. More specifically, a recombinant porcine fVIII lacking most of the B-domain has been produced and is currently being tested for clinical application as a substitute for porcine fVIII purified from pooled porcine plasma (U.S. Pat. No. 6,458,563 incorporated herein by reference). The terms applied to these products are HYATE:C (natural porcine fVIII partially purified from pooled porcine plasma); OBI-1 (for recombinant partially B-domainless porcine fVIII). OBI-1 is also termed POL-1212 in U.S. Pat. No. 6,458,563. Both names, OBI-1 and POL 1212, refer to the same substance, porcine fVIII having the B-domain deleted except for 12 amino acids at the N-terminal part of the B-domain and 12 amino acids at the C-terminal part of the B-domain. The DNA sequence encoding OBI-1 is given in SEQ ID No:1. The deduced amino acid sequence of OBI-1 protein is given in SEQ ID NO:2, along with that of the 19 amino acid leader (signal) peptide. OBI-1 is a protein having a deduced amino acid sequence of amino acids 1-1448 of SEQ ID NO: 2. OBI-1 protein is made by expression of the DNA of SEQ ID NO:1 in a transformed mammalian host cell, which results in removal of the signal peptide, amino acids −19 to 1 of SEQ ID NO:2, and secretion of the protein from the host cell into the cell culture supernatant. Therefore, OBI-1 is herein defined as the product of expression of the DNA of SEQ ID No: 1 in a mammalian host cell. Previous studies (Doering, C. B. et al. [2002] J. Biol. Chem. 277:39345-38349) have documented that the B-domain of porcine fVIII can be deleted without loss of activity.

There are several reports of various methods to provide stable fVIII in a pharmaceutical composition or formulation. Albumin has often been used to stabilize these formulations. However, because of the cost and risk associated with using albumin as a stabilizer, there are several albumin-free pharmaceutical compositions containing fVIII in the art. For example, U.S. Pat. No. 5,565,427 describes fVIII compositions which contain an amino acid or its salts and a detergent such as polysorbate or TWEEN 80, or an organic polymer such as PEG; U.S. Pat. No. 5,605,884 discloses a fVIII composition in a high ionic strength media consisting of sodium chloride, calcium chloride and histidine; U.S. Pat. Nos. 5,763,401 and 5,874,408 disclose a recombinant fVIII composition containing glycine, histidine, sucrose, sodium chloride, and calcium chloride. There are further examples of fVIII compositions having various salts, non-ionic surfactants and anti-oxidants (U.S. Pat. No. 5,962,650, U.S. Pat. No. 5,972,885, WO 89/09784, and WO 94/07510). WO 03/080108 describes a stable solid pharmaceutical composition devoid of amino acids which contain fVIII, a surfactant, calcium chloride, sucrose, sodium chloride, trisodium citrate, and a buffer and has a pH of 6-8 prior to lyophilization and after reconstitution in water for injection.

SUMMARY OF THE INVENTION

The present invention relates to the surprising experimental findings that OBI-1 as described, supra, has 2-6 fold greater bioavailability compared to HYATE:C. Bioavailability refers to the blood levels achieved and maintained after administering a given dose. Bioavailability can be assessed by calculating the area under the curve (AUC) of blood levels plotted as a function of time after administration of a given dose. Consequently, compared to HYATE:C, OBI-1 can be administered at a substantially lower dose, expressed in Units/kg of body weight, to provide equivalent protection against serious bleeding episodes or in the prevention of bleeding episodes for hemophiliac patients who are in non-bleeding state. Alternatively, OBI-1 can be provided at the same dose as, or a similar dose to, HYATE:C, but at a reduced frequency of administration compared to HYATE:C, bringing about more rapid control of bleeding and reducing the inconvenience associated with multiple administrations. Coupled with the fact that OBI-1 is available at a higher concentration in Units/ml than HYATE:C, the findings provide for a new method of administration that is highly advantageous for patients' well-being and quality of life. Current treatments with HYATE:C (100 Units/kg of body weight) typically require intravenous infusion of 280 ml of HYATE:C solution, at a rate of 2-5 ml per minute repeated every 6-8 hrs. Such treatments are tedious, can last 2 hours or more, and severely limit patient mobility and quality of life. By contrast, under the present invention, OBI-1 can be administered as a single intravenous injection of about 10-125 Units/kg body wt, at the rate of 1,000-10,000 Units/min. and may be required only one to four times, in order to halt a bleed, in contrast to HYATE:C, which takes a median of eight separate administrations over a two day period to halt a single bleeding episode, according to its package insert. When a hemophilia patient in need of such treatment has preexisting inhibitory antibodies to human fVIII that significantly cross-react with OBI-1, standard treatment, as applied using HYATE:C, would require more OBI-1 beyond the dosage given herein to neutralize the antibodies. Using OBI-1, faster control of bleeding is facilitated because higher fVIII levels can be achieved more rapidly. As will be discussed below, the actual dose administered to an individual depends on several individual factors including body weight, plasma volume, and residual antibody titer to OBI-1. The methods for calculating individual dosage have been well established from studies with HYATE:C. The methods for calculating OBI-1 dosage will, in addition, require taking into account the newly discovered greater in vivo efficacy and bioavailability of OBI-1. In an alternative embodiment of the invention, an antibody-neutralizing dose ("Loading Dose") is omitted altogether, allowing for faster control of bleeding than heretofore available when following a standard administration method.

The present invention also provides pharmaceutical compositions and kits containing OBI-1 that are useful for treating a patient in need of fVIII in a more rapid and effective manner than conventional treatment methods.

DETAILED DESCRIPTION OF THE INVENTION

Figure 1:
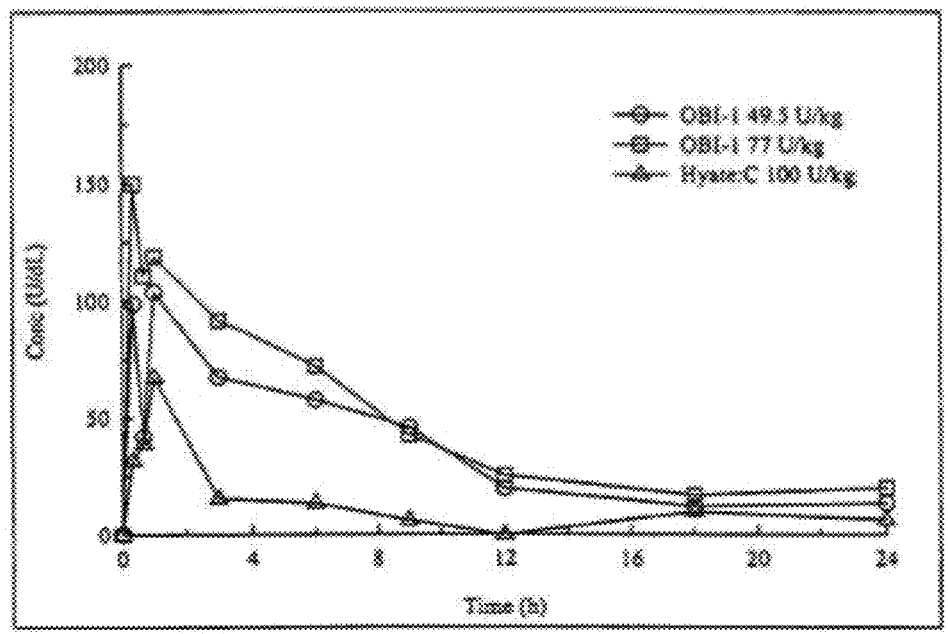
FIG. 1 is a graph of activity recoveries of fVIII (Example 1), corrected for baseline fVIII after a single injection of either HYATE:C or OBI-1 into cynomolgus monkeys at the indicated dose as described in Example 1.

In general, the terms and phrases used herein have their art-recognized meaning, which can be found by reference to standard texts, journal references and contexts known to those skilled in the art. The following definitions are provided to clarify their specific use in the context of the invention.

As used herein, OBI-1 is a recombinantly produced porcine fVIII derivative which lacks most of the B domain. The deduced amino acid sequence of OBI-1 is given in SEQ ID NO:2. See also U.S. Pat. No. 6,458,563. The term, "physiologically acceptable carrier," as used herein, is an organic or inorganic composition which serves as a carrier/stabilizer of the active ingredient of the present invention, OBI-1, in a pharmaceutical composition. Examples of physiologically acceptable carriers include but are not limited to water, phosphate-buffered saline, saline, aqueous solvents, where water is mixed with lower alkanols, vegetable oils, polyalkylene glycols, petroleum-based jelly, ethyl cellulose, ethyl oleate, carboxymethyl cellulose, polyvinylpyrrolidine, isopropyl myristate. Physiologically acceptable carriers further include albumin, an amino acid (e.g., glycine, histidine, or its salts), a detergent (ionic and non-ionic) such as polysorbate or TWEEN 80, a high ionic strength medium containing sodium salts, calcium salts and/or histidine, mono-, di- or polysaccharides (e.g., sucrose) or sugar alcohols, and other diluents, additives or carriers known in the art. For detailed description of various carriers and additives, see U.S. Pat. No. 5,925,739; U.S. Pat. No. 5,733,873; U.S. Pat. No. 5,605,884; U.S. Pat. No. 5,565,427; U.S. Pat. No. 5,763,401; U.S. Pat. No. 5,874,408; U.S. Pat. No. 5,962,650; U.S. Pat. No. 5,972,885; WO 89/09784 and WO 94/07510, all of which are incorporated by reference in their entireties to the extent there is no inconsistency with the present disclosure.

A pharmaceutical composition comprising OBI-1 is preferably a solid composition obtainable by lyophilization of a solution devoid of amino acids, the solution comprising OBI-1, a surfactant or detergent, calcium chloride, sucrose, sodium chloride, trisodium citrate and a buffer. The solution has a pH of 6-8 prior to lyophilization and after reconstitution in water for injection. The surfactant is preferably a non-ionic surfactant such as polysorbates and block copolymers like poloxamers (i.e., copolymers of polyethylene and propylene glycol). A more preferred surfactant is a polysorbate having a mean polymerization degree from 20 to 100 monomer units (preferably about 80). The most preferred surfactant is polysorbate 80 derived from a plant. The buffer is preferably tris(hydroxymethyl)methylamine, commonly known as "tris." Typically, the solid pharmaceutical composition is prepared by lyophilization from the solution containing OBI-1 at a concentration from 50 to 10,000 Units/mL, a surfactant at a concentration ranging from above critical micellar concentration to 1% v/v, calcium chloride at 0.5-10 mM, sucrose at 5-50 mM, sodium chloride at 0.15-0.5 M, trisodium citrate at 1-50 mM, and a buffer at 1-50 mM. The pH of the pharmaceutical composition prior to lyophilization and after reconstitution in water for injection is preferably about 6.5-7.5, more preferably about 7.0. The solid pharmaceutical composition containing OBI-1 may be diluted with sterile water optionally containing sodium chloride before administering into a patient in need of fVIII. The administration of such composition is typically carried out intravenously. The optimal dose of composition to be administered is determined by the treating physician based on the severity of the disease for each patient. WO 03/080108, which is incorporated herein as reference in its entirety, discloses a detailed description of a method of preparing a preferred solid pharmaceutical composition comprising OBI-1.

The term "about" refers to an interval around the considered value. As used in the present application, "about X" means an interval from X minus 10% of X to X plus 10% of X, and preferably an interval from X minus 5% of X to X plus 5% of X.

The phrase, "reducing blood clotting time" as used herein, refers to the reduced length of time for blood clotting to occur in a given patient having fVIII deficiency when OBI-1 is administered compared to when HYATE:C is administered, i.e., the difference in the length of time for blood clotting to occur in patients treated with OBI-1 and those treated with HYATE:C administration.

The term, "therapeutically effective level or concentration of factor VIII" as used herein, means the level of fVIII in the plasma of a patient having fVIII deficiency, who has received a pharmaceutical composition of OBI-1, that is sufficient to exhibit a measurable improvement or protective effect in the patient (e.g., to stop bleeding). The patients having fVIII deficiency are typically congenital hemophilia A patients but also include those subjects diagnosed with "acquired hemophilia", a condition in which those who are not congenital hemophiliacs spontaneously develop inhibitory antibodies to their fVIII, creating a serious fVIII deficiency. In general, the therapeutically effective level is estimated to be about 1%, preferably about 10%, most preferably about 25-35% and above, of the fVIII level in a normal, non-hemophilia A subject. The concentration range of fVIII in normal non-hemophilia A humans is defined as 50% to 200% of the fVIII activity found in a sample plasma pool derived from at least 20 normal donors. The level of fVIII in normal humans fluctuates through this normal range in response to various physiologic and non-physiologic stimuli (see Bithell, T C, "The Diagnostic Approach to the Bleeding Disorders", page 1302, Chapter 48 in Lee G R, Bithell T C, Foerster J, Athens J W and Lukens J N [eds], *Wintrobe's Clinical Hematology, ninth edition,* 1993, Lea & Febiger, Malvern, Pa.).

The phrase, "antibody-neutralizing dose of OBI-1," is used to indicate the amount of OBI-1 to administer to neutralize the patient's preexisting antibodies directed against OBI-1. The level of a hemophilia A patient's antibody to porcine fVIII is different for each individual. The amount of anti-OBI-1 antibody present can be readily calculated by measuring the antibody titer, using standard methods known in the art, and from this value, the amount of OBI-1 required to neutralize the antibody can be estimated. Because of individually differing binding and inactivating characteristics of each patient's inhibitory antibody, the precise amount of OBI-1 required can only be estimated, and the exact amount to be administered must be empirically determined (or "titrated").

Human fVIII deficiency can be studied in fVIII-deficient mammals because the steps of blood clot formation are shared among all vertebrates, and fVIII proteins of several species are known to have a high degree of sequence homology. Bioavailability can also be assessed in non-hemophilic monkeys. After taking into account species variations in blood volume, basal fVIII levels and the like, results from animal studies are generally predictive of results in humans. The present invention was developed from results of experiments, described in detail below. Studies of five types were conducted: bioavailability studies in monkeys and hemophilic dogs, efficacy studies in hemophilic dogs and hemophilic mice, an in vitro activity recovery study in human plasma, and an in vivo bioavailability studies in six human subjects, and clinical efficacy in four human patients with a total of ten bleeding episodes.

Bioavailability was assessed by measuring recovery of activity at a specified time after administering a given dose. Efficacy was assessed by measuring the effect of a given dose on the cuticle bleeding time (CBT) in hemophilic dogs and by mortality in a tail-transection-bleeding model of hemophilic mice. Recoveries of OBI-1 and the HYATE:C were also measured in vitro by adding each substance to human hemophilic plasma samples and human hemophilic-inhibitor plasma samples. Bioavailability was further assessed in six human subjects by measuring recovery of activity at a specified time after administering a standard dose of 100 U/kg. Clinical efficacy was evaluated following a standard treatment protocol by investigation and patient evaluation of cessation of bleeding.

In initial studies of activity recovery (bioavailability), non-hemophilic monkeys were given OBI-1 or HYATE:C intravenously to raise fVIII levels in their blood. Blood samples were taken periodically to determine fVIII activity and persistence of the product in the animal's bloodstream over time. Bioavailability of OBI-1 was found to be several-fold greater than HYATE:C (see Tables 1 and 2, and FIG. 1). Similar differences were observed between HYATE:C and OBI-1 in bioavailability studies in hemophilic dogs as shown in Tables 3 and 4.

In one efficacy study, hemophilic dogs were tested for bleeding times after a toenail cuticle clip, using a range of OBI-1 or HYATE:C doses. The cuticle bleeding times (CBTs) were measured to evaluate the efficacy of the fVIII products. Both the OBI-1 and HYATE:C reduced CBT towards the normal range observed in non-hemophilic dogs, although the results were variable. Consistent with the mouse studies as described below, OBI-1, on a comparable unit basis, appeared to be more effective at reducing the CBT than did HYATE:C.

Efficacy studies were further carried out with a strain of fVIII "knockout" mice: mice in which the gene encoding fVIII was inactivated. Such mice are highly susceptible to hemorrhage following even trivial injury. Transection of the distal 2 cm of the tail will lead to fatal hemorrhage within 24 h for most of the hemophilic mice. By administering a dose range of OBI-1 or HYATE:C to the hemophilic mice 15 minutes before tail transection, it was possible to estimate a dose which protects 50% of the mice from mortality ($ED_{50}$). In these studies in which OBI-1 and HYATE:C were separately tested, the $ED_{50}$ (units/kg) of OBI-1 appeared to be roughly one-fourth that of HYATE:C as can be seen in Tables 6 and 7.

In experiments using hemophilic mice and dogs, comparable doses of OBI-1 and HYATE:C resulted in greater recovery of OBI-1 than HYATE:C based on a standard fVIII clotting assay.

The accumulated results indicate that OBI-1 can be administered at a significantly lower effective dose than can HYATE:C, where the activity level of each has been measured by a standard fVIII assay. It will be understood by those skilled in the art that the effective dose can be calibrated according to individual patient requirements, including residual levels of fVIII existing in the patient's plasma and the level of inhibitory antibodies in the patient's plasma that must be neutralized.

Recoveries of OBI-1 and the HYATE:C also were measured in vitro after adding each to a nominal concentration of 1 U/ml to human plasma samples from hemophilia patients with inhibitory antibodies. Recoveries of both OBI-1 and HYATE:C were lower than the nominal concentration, which was due in part to cross-reactive inhibitory antibodies. However, in 25 of 35 samples, recovered OBI-1 activity was greater than recovered HYATE:C activity, and in 18 of the 35 samples, recovered OBI-1 activity was more than 2-fold greater than recovered HYATE:C activity.

Bioavailability studies were further carried out in six human subjects, with absent or minimal inhibitory antibodies to OBI-1, in a randomized, double-blind, double-dummy, parallel-group blinded manner as described in Example 6. As shown in Table 8 and FIGS. 3 and 4, the bioavailability of OBI-1 was much greater than HYATE:C when both were administered at 100 U/kg.

The substantially greater recovery and bioavailability of OBI-1 compared to HYATE:C is surprising, and it can neither be predicted nor explained by the fact that OBI-1 is a recombinant product and HYATE:C is a plasma derived product. In fact, with human factor IX (used in the treatment of hemophilia B), the plasma derived product actually showed recoveries about two times greater than the recombinant derived product (1.71+/−0.73 IU per dL per IU per kg compared to 0.86+/−0.313 IU per dL per IU per kg) (see Ewenstein B M et al. *Transfusion* [2002], 42:190). Equally important, when the bioavailability of a B-domain deleted recombinant human fVIII product was compared to that of a plasma derived human fVIII product, the two products were found to be bioequivalent. (See Kessler, C M, et al. *Hemophilia* [2005], 11:84.)

The clinical results for OBI-1 and HYATE:C are consistent with the pharmacokinetic data obtained using monkeys, hemophilic dogs, and hemophilic mice. These results further indicate that OBI-1 can be administered at a lower dose or equally important can be administered at a greatly reduced frequency of administration, compared to HYATE:C, to yield equivalent therapeutic effects in patients having fVIII deficiency. The data also show that OBI-1 reaches peak and therapeutic levels much more rapidly than equivalent doses of HYATE:C, allowing for more rapid control of bleeding. Consistent with the foregoing, but in a departure from previously standard practice, effective control of a bleeding episode can be obtained with a single treatment dose of OBI-1 in a patient with anti-OBI-1 antibodies, in the absence of administration of an antibody-neutralizing Loading Dose.

EXAMPLES

Example 1

Bioavailability Study in Monkeys

Non-hemophilic cynomolgus monkeys were used to compare bioavailability of OBI-1 and HYATE:C. Groups of 4 monkeys were given one intravenous dose of either HYATE:C 100 U/kg, or OBI-1 at doses of either 49 or 77 U/kg. Blood samples were drawn at specified time points thereafter, and the fVIII levels obtained were used to calculate pharmacokinetic parameters, including the activity levels integrated over time. The integrated value is referred to as area under the curve for the specified time period ($AUC_{0\rightarrow t}$).

Pharmacokinetic analyses were calculated using non-compartmental methods, corrected for baseline (endogenous fVIII level in the test animal). The maximum plasma concentration, Cmax, and the time to maximum plasma concentration, Tmax, were taken directly from the data. The area under the curve from time zero to the final sample ($AUC_{0+t}$) was calculated using the linear trapezoidal method. The results are shown in FIG. 1.

There was a dose proportional increase in Cmax and $AUC_{0\rightarrow t}$ between the two doses of OBI-1. Mean plasma fVIII levels for monkeys receiving HYATE:C 100 U/kg were lower than the fVIII levels of monkeys receiving OBI-1, at both 49.5 and 77 U/kg, at every time point but one. Biological availability (AUC) of HYATE:C 100 U/kg (299±191 h·U/dL), was only approximately ⅓ that of OBI-1 given at a dose of 49.5 U/kg (900±311 h·U/dL) and one-quarter that of OBI-1 given at a dose of 77 U/kg (1178±669 h·U/dL). At one time point, 0.66 hours, the fVIII levels measured appeared spurious for several animals, likely due to mishandling of the plasma specimens. Calculating the pharmacokinetic values excluding the fVIII values at 0.66 hours for the analysis resulted only in very minor changes to $AUC_{0\rightarrow 24}$.

Table 1 sets forth Pharmacokinetic Parameters for Baseline Corrected fVIII Levels After iv Administration of HYATE:C and OBI-1 in Monkeys.

TABLE 1

| Parameter[1] | OBI-1 49.5 U/kg | OBI-1 77 U/kg | HYATE:C 100 U/kg |
|---|---|---|---|
| Cmax (U/dL) | 107 ± 22.6 | 169 ± 32.2 | 78.7 ± 20.4 |
| Tmax (h) | 2.00 | 1.98 | 2.22 |
| $AUC_{0\rightarrow 24}$ (h·U/dL) | 900 ± 311 | 1,178 ± 669 | 299 ± 191 |

[1]Arithmetic mean ± standard deviation except for Tmax for which the median is reported.

In conclusion, OBI-1 administered intravenously to cynomolgus monkeys in a dose of 49.5 U/kg or 77 U/kg, resulted in a much greater area under the time-concentration curve than did a dose of HYATE:C at 100 U/kg. This serendipitous finding reveals an unpredictable difference between OBI-1 and HYATE:C, specifically that OBI-1 displays an enhanced in vivo activity when administered into monkeys, compared with HYATE:C. When the data of Table 1 are compared on an equivalent U/kg basis it can be seen that a 49.5 U/kg dose of OBI-1 provided about 6-fold greater $AUC_{0\rightarrow 24}$ than did a 100 U/kg dose of HYATE:C. A 77 U/kg dose of OBI-1 provided about 5-fold greater $AUC_{0\rightarrow 24}$ than did 100 U/kg of HYATE:C. Similar results were obtained in a separate study using five monkeys receiving 40 U/kg OBI-1, 5 monkeys receiving 100 U/kg OBI-1 and 6 monkeys receiving 100 U/kg HYATE:C. (Table 2.)

TABLE 2

Pharmacokinetic Parameters for Baseline-Corrected Factor VIII After i.v. Administration of OBI-1 and HYATE:C in Monkeys.

| Parameter[1] | OBI-1 40 U/kg | OBI-1 100 U/kg | HYATE:C 100 U/kg |
|---|---|---|---|
| Day 1 | | | |
| Cmax (U/dL) | 73.4 ± 9.24 | 230 ± 66.5 | 101 ± 28.0 |
| Tmax (h) | 0.50 | 0.50 | 0.50 |
| $AUC_{0\rightarrow 12}$ (h·U/dL) | 323 ± 120 | 1,604 ± 857 | 607 ± 304 |
| Day 4 | | | |
| Cmax (U/dL) | 71.2 ± 62.3 | 153 ± 20.1 | 89.3 ± 24.7 |
| Tmax (h) | 0.50 | 0.53 | 0.50 |
| $AUC_{0\rightarrow 12}$ (h·U/dL) | 353 ± 538 | 542 ± 256 | 193 ± 185 |

[1]Arithmetic mean ± standard deviation except for Tmax for which the median is reported.

Example 2

Bioavailability in Hemophilic Dogs

Originally discovered as a spontaneous mutation, dogs with hemophilia A have been maintained in a protected colony for over twenty years. The colony housed at the Queens University in Kingston, Ontario, is in its tenth generation. They have no circulating fVIII activity or protein and their phenotypic picture is analogous to severe hemophilia A in humans, with recurrent severe spontaneous soft tissue and joint bleeds and chronic joint deformities. They require frequent injections of canine-derived plasma or cryoprecipitate to control their bleeding.

Eight healthy dogs aged 6 months or greater, weighing at least 6 kg and lacking anti-porcine fVIII antibody were each administered a single intravenous dose of either HYATE:C or OBI-1. Two animals each received 3 U/kg, 25 U/kg, or 100 U/kg of each product. Blood samples were drawn at baseline and at the following time points after the injection of the products: 0.25, 0.5, 1, 2, 4, 8, 12, 24, 36, 48 and 72 hours. FVIII levels were determined by both one-stage clotting assay and chromogenic assay methods.

FVIII levels were determined against a porcine fVIII standard designated HY98P. Although these hemophilic dogs have no measurable canine fVIII activity, and no fVIII antigen present in their blood, they were found to have measurable fVIII activity at baseline (0.1 to 0.3 U/ml) when tested against a porcine fVIII standard. This porcine standard was made by adding varying amounts of the actual test product HYATE:C or OBI-1 (in 1% bovine serum albumin/imidazole buffer) to factor VIII deficient human hemophilic plasma. For purposes of determining pharmacokinetic parameters, therefore, the baseline activity measured was subtracted from the measured activity at each time point and the difference in fVIII activity was entered for all calculations. For both products tested, there was substantial variability in the pharmacokinetic values obtained from the dogs tested at each dose level.

Mean values for selected pharmacokinetic parameters are shown in Table 3 (Chromogenic Assay) and Table 4 (One-Stage Clotting Assay).

TABLE 3

Bioavailability in hemophilic dogs: Chromogenic Assay

| DOSE (U/kg) | | | Recovery | AUC | Cmax | | Recovery | AUC | Cmax |
|---|---|---|---|---|---|---|---|---|---|
| 100 U/kg | mean | OBI-1 | 4.73 | 22.21 | 4.73 | HYATE:C | 1.80 | 9.31 | 1.80 |
| | Std. Dev. | | 0.68 | 8.20 | 0.68 | | 0.32 | 1.94 | 0.32 |
| 25 U/kg | mean | | 4.97 | 35.15 | 1.24 | | 1.46 | 2.63 | 0.37 |
| | Std. Dev. | | 0.88 | 39.26 | 0.23 | | 0.28 | 1.24 | 0.06 |
| 3 U/kg | mean | | 6.65 | 1.14 | 0.20 | | 2.38 | 0.35 | 0.08 |
| | Std. Dev. | | 0.40 | 0.01 | 0.01 | | 0.21 | 0.34 | 0.01 |

TABLE 4

Bioavailability in Hemophilic Dogs: One-Stage Clotting Assay

| DOSE (U/kg) | | | Recovery | AUC | Cmax | | Recovery | AUC | Cmax |
|---|---|---|---|---|---|---|---|---|---|
| 100 U/kg | mean | OBI-1 | 4.24 | 30.89 | 4.41 | HYATE:C | 1.95 | 14.11 | 1.95 |
| | Std. Dev. | | 1.45 | 15.00 | 1.41 | | 0.28 | 5.81 | 0.29 |
| 25 U/kg | mean | | 3.12 | 11.92 | 0.86 | | 1.72 | 4.75 | 0.43 |
| | Std. Dev. | | 0.79 | 2.40 | 0.22 | | 0.68 | 2.08 | 0.17 |
| 3 U/kg | mean | | 3.74 | 1.80 | 0.12 | | 3.00 | 2.27 | 0.09 |
| | Std. Dev. | | 1.41 | 1.03 | 0.05 | | 1.67 | 1.52 | 0.05 |

The results of the clotting assay and chromogenic assay were similar. Maximum Concentration (Cmax) in the blood for OBI-1 was greater than for HYATE:C at all doses. The mean Time to Maximum Concentration (Tmax) was shorter for OBI-1 than it was for HYATE:C at 3 and 25 U/kg doses but the opposite was seen at a dose of 100 U/kg. Mean Recovery percentage was greater for OBI-1 than for HYATE:C at all doses: at 25 and 100 U/kg, recovery values for OBI-1 were approximately 2-5 times that of HYATE:C. For Area Under the Curve, regardless of treatment group the geometric mean of AUC increased as the dose increased. Overall the pharmacokinetic values as measured by the two assay methods, the one-stage clotting and the chromogenic assays, followed the same trends across most parameters.

Example 3

Efficacy in Hemophilic Dogs

CBT, the time it takes for bleeding to stop after the dog's toenail cuticle is cut, is a useful measure of efficacy in hemophilia dogs. In the untreated dog with hemophilia, the cuticle usually stops bleeding in approximately 2 minutes, does not bleed for a brief time and then re-bleeds steadily for at least 12 minutes or until the lesion is cauterized. The normal CBT is defined as 5 or fewer minutes of bleeding and no need for cauterization. CBT in dogs with congenital hemophilia has been used widely as a measure of the efficacy of investigational fVIII products.

The experimental design was that described in Example 2.

Table 5 demonstrates the individual changes in the CBT results for each dog for each injection.

TABLE 5

Effect of Porcine fVIII Products on Dog Cuticle Bleeding Times

| | | CBT after OBI-1 minutes | | | CBT after HYATE:C minutes | | |
|---|---|---|---|---|---|---|---|
| Dog | Dose U/kg | Pre injection | Post injection | Reduction | Pre injection | Post injection | Reduction |
| Becky | 3 | 8.5 | 12 | −3.5 | | | |
| Hamish | 3 | 11 | 4 | 7 | 8 | 10 | −2 |
| Zoey A | 3 | 12 | 12 | 0 | 12 | 12 | 0 |
| Mindy | 25 | 9 | 3 | 6 | 8 | 6 | 2 |
| Java | 25 | 13 | 6 | 7 | 2 | 4 | −2 |
| Wendel | 100 | 12 | 9.5 | 2.5 | 12 | 12 | 0 |
| Arsenio A | 100 | 12 | 2 | 10 | 4 | 5 | −1 |
| Arsenio B | 100 | 11 | 1 | 10 | 6 | 2 | 4 |
| Zoey B | 100 | 12 | 8* | 4 | 12 | 3 | 9 |
| Mean Reduction, minutes | | | | 4.78 | | | 1.25 |
| S.D. | | | | 4.51 | | | 3.73 |

*In Zoey-2 (second study) the cuticle bleeding was extremely slow after the 2 min point with only 1-2 drops/min up to 8 min when bleeding stopped completely.

Although there was substantial variation between individual dogs, the data indicate greater in vivo efficacy in dogs given OBI-1. The mean reduction in CBT over all doses in the OBI-1 in HYATE:C dogs was 4.78 min and 1.25 min respectively. This difference was not statistically significant, but there was a trend toward significance (p=0.10, t test). The difference between the efficacy of OBI-1 and HYATE:C was more pronounced at the lower doses of 3 U/kg and 25 U/kg, where OBI-1 reduced the CBT in some dogs but HYATE:C did not.

Example 4

Mouse Efficacy Study

Hemophilia A mice have been created by targeted disruption of exon 16 of the fVIII gene. The E16 mice have undetectable fVIII activity, occasional spontaneous bleeding, and prolonged bleeding and increased mortality after tail transection or laceration of the tail vein. An efficacy model has been developed in which the ability of fVIII to decrease the mortality in E16 mice following transection of the distal 2 cm of tail is assessed.

Research grade OBI-1 was prepared by expressing the OBI-1 cDNA in a baby hamster kidney cell line and purification from serum-free expression medium using a two-step chromatography procedure as described in Doering et al. (2002) J. Biol. Chem. 277:38345-9. The following experiment was designed to test the efficacy of OBI-1 in the tail transection model.

Male or female hemophilia A mice, aged 9 to 10 weeks, were injected in the tail vein with various concentrations of OBI-1 or control buffer. The mice were anesthetized and, 15 min after injection, the distal 2 cm of tail was transected and allowed to bleed freely. This injury reportedly is fatal within 24 h in most E16 hemophilia A mice.

Survival at 24 h was determined with the following results:

TABLE 6

Efficacy of OBI-1 in Hemophilia A Mice: Tail Transection Model Survival

| Dose (U/kg) | (Alive/Total) | Survival (%) |
| --- | --- | --- |
| 0.0 | 6/38 | 16 |
| 0.015 | 2/8 | 25 |
| 0.044 | 5/7 | 71 |
| 0.130 | 4/7 | 57 |
| 0.400 | 7/7 | 100 |
| 1.200 | 7/7 | 100 |
| >1.200 | 14/14 | 100 |

The data are consistent with the statement that a dose of fVIII of 1.2 Units/kg is effective in preventing death in this model. Combining the data at 0.4 and 1.2 Units/kg, there are 14/14 survivors compared to 6/38 survivors in the control (untreated) group. An estimated dose conferring 50% survival ($ED_{50}$) was 0.044 U/kg. Furthermore, every mouse receiving at least 0.4 U/kg survived.

Efficacy of HYATE:C in Hemophilia Mice

Prior to tail vein injections of HYATE:C (0 to 100 fVIII Units/kg), or placebo (saline), mice were warmed under a 60-watt lamp for 2 minutes to dilate the tail veins. Fifteen minutes after injection, mice were anesthetized with Metofane and the distal 2 cm of the tail was amputated. Mice were placed into clean cages with paper towels in place of litter and observed for 24 hours to determine survival. Well-moistened food was placed inside each cage in addition to the usual water bottle and dry pellets. Survivors were terminated after 24 hours using Metofane followed by cervical dislocation.

There was a dose-dependent increase in survival in both treated groups following injection of product (Table 7).

TABLE 7

Efficacy of HYATE:C in Hemophilia A Mice Survival

| Dose (U/kg) | (Alive/Total) | Survival (%) |
| --- | --- | --- |
| 0.0 | 2/17 | 11 |
| 0.3 | 4/8 | 50 |
| 0.1 | 5/17 | 30 |
| 0.2 | 5/10 | 50 |
| 0.5 | 16/20 | 80 |
| 1.0 | 7/10 | 70 |
| 2.0 | 14/18 | 78 |
| 5.0 | 9/10 | 90 |
| 8.0 | 8/8 | 100 |
| 10.0 | 10/10 | 100 |
| 25.0 | 2/2 | 100 |
| 50.0 | 2/2 | 100 |
| 75.0 | 1/1 | 100 |
| 100.0 | 2/2 | 100 |

The estimated $ED_{50}$ for HYATE:C was 0.2 U/kg, 4-5 times greater than that estimated for OBI-1, predicting greater efficacy of OBI-1. Overall, the comparative efficacy of HYATE:C and OBI-1 has not been rigorously studied in hemophilia A mice.

Example 5

Recovery from Human Plasma

Materials

Citrated pooled normal human plasma (FACT, product No. 0020-0) and fVIII-deficient plasma (human hemophilia A plasma, product no. 0800) were purchased from George King Bio-medical, Inc.). The pooled plasma samples were stored at −70° C. Activated partial thromboplastin time (aPTT) reagent (product No. 35513) was purchased from Organon Teknika Corp. It was stored in a lyophilized state at 4° C. OBI-1 Vehicle, Lot No. 214-02-001, was reconstituted with 1 ml Water for Injection per vial (60 vials total). Four vials of OBI-1, Lot No. 214-01-001, were each reconstituted with 1 ml Water for Injection, yielding an expected concentration of 550 U/ml according to the manufacturer's label. OBI-1 was diluted 15.9-fold further by addition of 59.6 ml of reconstituted OBI-1 vehicle, yielding a predicted concentration of 34.6 U/ml. Three vials of HYATE:C, Lot No. 656, were reconstituted with 20 ml Water for Injection, yielding an expected concentration of 34.6 U/ml, according to the manufacturer's label. HYATE:C was sub-aliquoted into 120 aliquots of 0.5 ml each and frozen at −70° C. OBI-1 was sub-aliquoted into 127 aliquots of 0.5 ml each and frozen at −70° C.

Citrated plasmas from patients with inhibitory antibodies to fVIII were shipped on dry ice to Emory University from several hemophilia treatment centers. Samples were frozen at −70° C. until used. From 58 plasma samples that were obtained, 25 were randomly selected for study.

FVIII Assays

FVIII one-stage clotting assays were performed using a Diagnostica Stago, ST art 4 Coagulation Instrument. Lyophilized aPTT reagent was solubilized in 3 ml $H_2O$ according to the manufacturer's instructions and kept at room temperature until used. FACT and fVIII-deficient plasma were stored on ice after rapid thawing in a 37° C. water bath. FVIII-deficient plasma (50 µl) was added to sample cuvettes and allowed to warm for 30-45 seconds before addition of the remaining reagents. Dilutions of the fVIII standard or sample (5 µl) were added, followed by addition of 50 µl aPTT reagent and incubation for 250 seconds. Clotting was initiated by addition of 50 μl pre-warmed CaCl$_2$ solution using a cabled pipette. The addition activates an internal timer and records the clotting time in seconds. A standard curve was prepared using four dilutions of FACT into Hank's Buffered Saline: undiluted, ⅓, ¹⁄₁₁, and ¹⁄₂₁. The fVIII concentration of undiluted FACT is approximately 1 U/ml and ranged from 1.04 to 1.09 U/ml according to the manufacturer. The clotting time was plotted versus the logarithm of the fVIII concentration and the standard curve was calculated by linear regression. The fVIII concentration of samples was measured by interpolation on the standard curve, except in the case of analysis of stock solutions of OBI-1 and HYATE:C, for which more extensive measurements were made, as described in Results.

Figure 2:
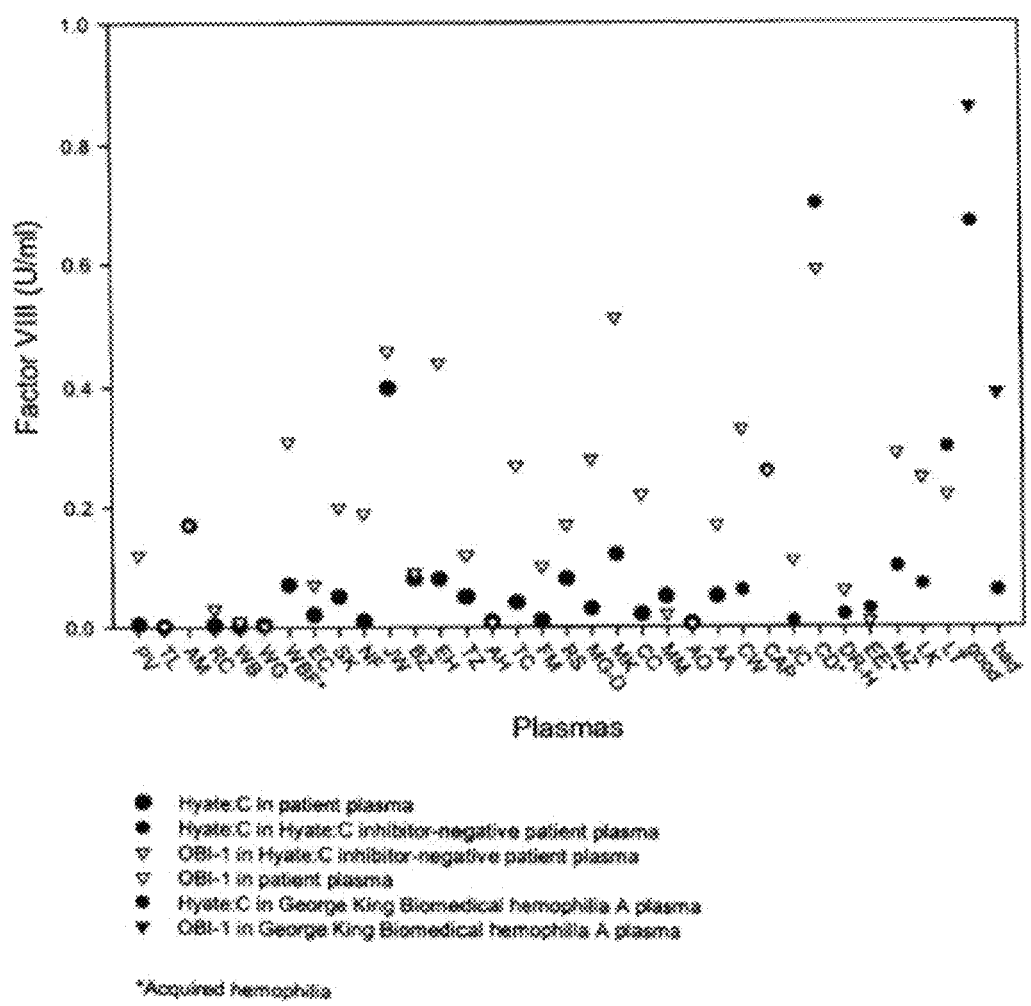
FIG. 2 is a graph of results obtained from the experiment described in Example 5. Individual patient plasmas are arrayed along the horizontal axis. The vertical axis indicates U/ml of fVIII activity recovered from the individual plasmas after addition of fVIII as described in Example 5. The data for King George Biomedical plasmas are designated as "good" or "bad" based on anomalous behavior of the latter plasma (see Example 5).

Reconstitution of fVIII activity from plasmas spiked with OBI-1 or HYATE:C was measured in 33 of the available inhibitor plasma samples (FIG. 2). In all cases, the plasmas were spiked to a predicted fVIII activity of 0.9 U/ml. Additionally, two hemophilia A plasmas obtained from George King were included, and are shown at the far right in the figure. "Good" plasma corresponds to commercially available reagent plasma in which recovery of fVIII in HYATE:C and OBI-1 had previously been found to be in the expected range. "Bad" plasma corresponds to plasma in which recovery of fVIII in HYATE:C had previously been found to be less than 10% of expected at Ipsen. The results confirm that the expected recovery of OBI-1 is obtained in the "good" plasma and that the recovery of HYATE:C is close to the expected range. However, recovery of activity from the "bad" plasma spiked with HYATE:C again was observed to be quite poor. Recovery of OBI-1 from this plasma was considerably higher, but lower than expected.

Recovery of fVIII activity in the inhibitor patient plasmas was very low, less than 0.1 U/ml in almost every single HYATE:C spiked plasmas. Recovery was significantly higher when these same plasmas were spiked with OBI-1, but was lower than expected (because of the presence of inhibitor antibodies). Several of the plasmas that had previously been assayed as negative for inhibitory antibodies to HYATE:C were assayed and are shown in FIG. 2. The recovery of HYATE:C was poor in most of these samples. This raised the possibility that a longer incubation time of HYATE:C with hemophilia A plasma, such as occurs during the 2 hour incubation in the Bethesda assay, might lead to increased recovery of activity of HYATE:C. However, when HYATE:C was added to one of the HYATE:C-inhibitor negative patient samples, there was no increase of activity over 2 hours.

In conclusion, when OBI-1 is introduced into human plasma, whether or not it contains an inhibitor antibody to human fVIII, recovery in vitro is greater than that of HYATE:C The implication of this finding is that one can achieve the same circulating level of fVIII in a patient by administering a much lower dose of OBI-1 than of HYATE:C.

Example 6

Pharmacokinetics of OBI-1 versus HYATE:C in Human Subjects

To evaluate various pharmacokinetic parameters of OBI-1 versus HYATE:C in human subjects, the following randomized, parallel-group blinded comparison study was carried out with nine human patients. Of these 9 patients, five had no detectable anti-porcine inhibitor at baseline (i.e. less than 0.8 Bethesda units) and one (assigned to the OBI-1 group) had a very low inhibitor of 1.0 Bethesda units. Of the six patients with either no preexisting inhibitor or a very low inhibitor to porcine fVIII, three received HYATE:C and three received OBI-1. The three patients with significantly higher levels of inhibitors were excluded from the bioavailability assessment, as the presence of such inhibitors depresses bioavailability, thereby confounding the analysis. All patients were older than 12 years of age, were clinically diagnosed of hemophilia A, and were currently in the non-bleeding state. OBI-1 was provided in sterile vials containing 535 Units of fVIII activity per vial. Each vial was reconstituted with 1.0 ml Sterile Water for Injection USP to a final concentration of 535 U/ml. HYATE:C was provided in sterile vials containing 541 IU of fVIII per vial. Each vial was reconstituted with 20 ml Sterile Water for Injection USP to a final concentration of 27 IU/ml. The dose of each product administered was 100 IU/kg regardless of subject antibody titer. Investigators, patients and Sponsor were blinded to which patient received which active product, in a double-blind, double-dummy design. The patients received either 100 IU/kg of active HYATE:C followed by a placebo (three patients), or a placebo followed by 100 IU/kg of active OBI-1 (three patients), while in a stable, non-bleeding state. Each patient received an infusion over approximately one hour of the first product (HYATE:C or placebo of the same volume) followed by a slow push infusion from a syringe cover over 10 minutes of the second product (OBI-1 or placebo of the same volume).

Blood samples were drawn at times 0 (pre-injection), 20, 40, 60, 65, 75, 85, 105, and 125 minutes, and 3, 6, 9, 24, 27, 30 and 48 hours after the first infusion for determination of plasma fVIII activity levels both by one-stage clotting and chromogenic assay methods, using human pooled plasma as a fVIII standard. From these levels, standard pharmacokinetic analyses were performed and the results are shown in Table 8 and FIGS. 3 and 4. The pharmacokinetic parameters measured in this study include Clearance (CL, ml/h/kg), Area Under the Curve (AUC, U/dL), Maximum Concentration (Cmax, U/dL), Volume of distribution (Vz), mean time to maximum concentration (Tmax, h), and half-time ($T_{1/2}$, h).

TABLE 8

Summary of pharmacokinetic parameters for fVIII after intravenous administration of OBI-1 or HYATE:C to human patients.

| Parameter[1,2] | Activity Assay | | Chromogenic Assay | |
|---|---|---|---|---|
| | OBI-1 | HYATE:C | OBI-1 | HYATE:C |
| Cmax (U/dL) | 176 ± 88.0 | 82.3 ± 19.2 | 151 ± 31.5 | 52.7 ± 13.8 |
| Tmax (h) | 0.63 | 1.93 | 0.62 | 1.50 |
| AUC (0–6t) (h×U/dL) | 2,083 ± 1,323 | 1,178 ± 469 | 1,817 ± 625 | 708 ± 420 |
| AUC (inf) (h×U/dL) | 2,189 ± 1,396 | 967 ± 355 | 1,897 ± 605 | 771 ± 480 |
| t2 (h) | 10.3 ± 1.85 | 6.80 ± 2.19 | 10.5 ± 3.38 | 9.45 ± 5.14 |
| CL (mL/min) | 9.11 ± 6.31 | 11.8 ± 1.44 | 8.00 ± 2.61 | 17.3 ± 8.90 |
| (mL/min/kg) | 0.12 ± 0.11 | 0.18 ± 0.07 | 0.10 ± 0.04 | 0.27 ± 0.13 |
| Vz (L) | 7.55 ± 4.04 | 6.83 ± 1.40 | 7.51 ± 3.95 | 11.6 ± 2.21 |
| (L/kg) | 0.10 ± 0.07 | 0.10 ± 0.00 | 0.09 ± 0.07 | 0.18 ± 0.02 |

[1]Mean ± standard deviation except for Tmax for which the median is reported.
[2]N = 3 for both products.

Figure 3:
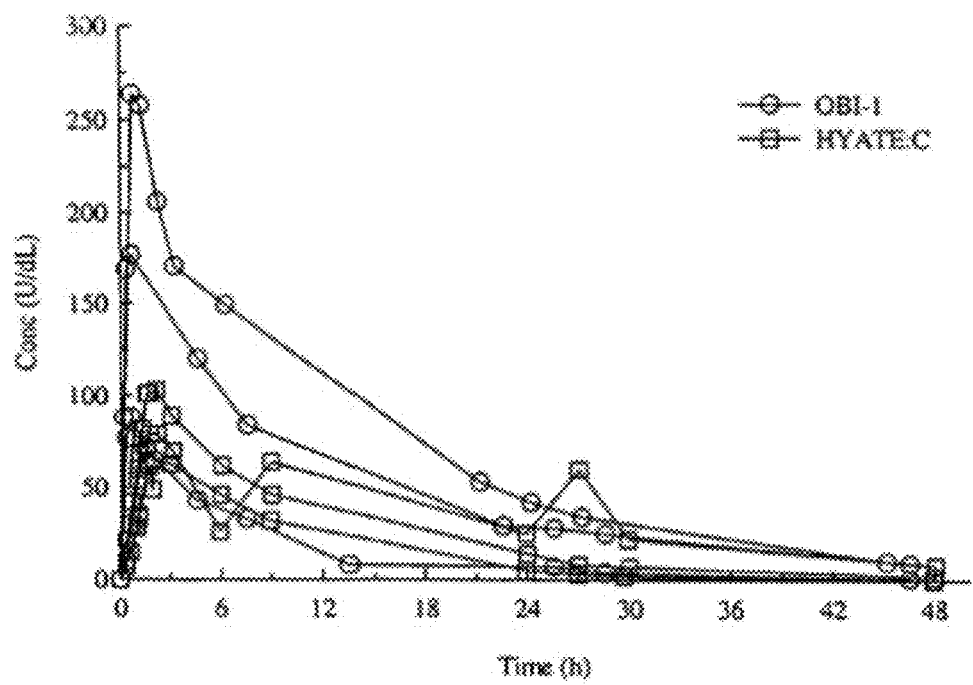
FIG. 3 is a graph showing the plasma concentrations of fVIII in six human patients after intravenous administration of OBI-1 or HYATE:C. The Y axis indicates U/ml of fVIII activity recovered from the individual plasmas as measured by the one-stage activity assay.
Figure 4:
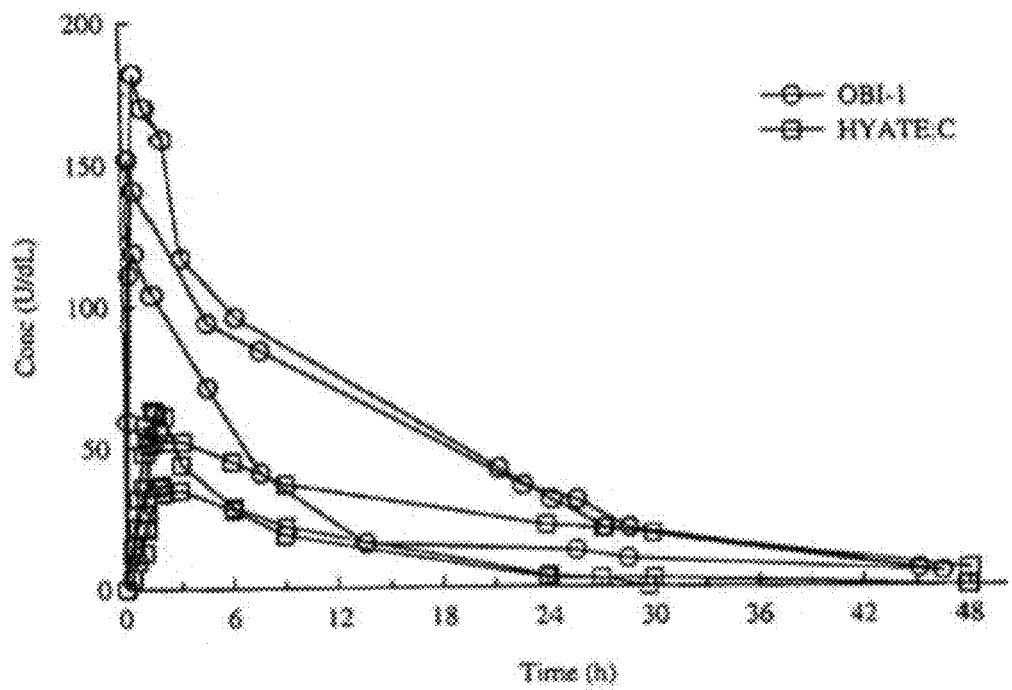
FIG. 4 is a graph showing the plasma concentrations of fVIII in six human patients after intravenous administration of OBI-1 or HYATE:C. The Y axis indicates U/ml of fVIII activity recovered from the individual plasmas as measured by the chromogenic assay as described herein.

As can be seen in Table 8 and FIGS. 3 and 4, the AUC values for OBI-1 were about 2-2.5 times greater than that for HYATE:C. The difference in AUC between OBI-1 and HYATE:C was more pronounced in the chromogenic assay than the one-stage activity assay. Maximum concentration (Cmax) in the blood for OBI-1 was about 3 times greater than for HYATE:C (151 vs 53 by the chromogenic assay). The mean time to Maximum Concentration (Tmax) was approximately 2.5 to 3 times shorter for OBI-1 than it was for HYATE:C. These results are consistent with the previous pharmacokinetic data obtained using monkeys, hemophilic dogs, and hemophilic mice, and further demonstrates that OBI-1 has much greater bioavailability compared to HYATE:C. Therefore, OBI-1 can be administered at a lower dose or be administered at a reduced frequency of administration, compared to HYATE:C, to yield equivalent therapeutic effects in fVIII deficient patients. OBI-1 at equivalent doses to Hyate:C can bring more rapid control of bleeding.

Example 7

Clinical Significance of the Differences in Recovery Values for OBI-1 and HYATE:C The studies disclosed above demonstrate that the recovery from human plasma, maximum concentration (Cmax), and the area under the curve (AUC) were much higher for recombinant porcine fVIII B-domain-deleted (OBI-1) than for plasma derived porcine fVIII (HYATE:C) after injection of the same doses.

The fVIII concentration in normal non-hemophilia A subjects is approximately 100 Units/dL. A typical bleeding episode is very likely to be controlled if the plasma level of fVIII is reached at about 25% and 35% of the normal level and maintained for several hours (Roberts H and Hoffman M, "Hemophilia A and Hemophilia B," Chapter 123 in Beutler E, Lichtman M, Coller B, Kipps T and Seligsohn U [Eds], *Williams Hematology*, $6^{th}$ edition [2001]: pages 1639-1657; McGraw-Hill, N.Y.). Using the pharmacokinetic data obtained from those subjects with no or low inhibitor to porcine FVIII (OBI-1, n=3; HYATE:C, n=3 as described in Example 6), additional calculations were performed to determine the pharmacokinetic values of OBI-1 and HYATE:C administration that correspond to the therapeutic levels of fVIII (i.e., 25-35%). The results are shown in Table 9.

TABLE 9

Calculated pharmacokinetic values corresponding to therapeutic levels of fVIII with OBI-1 and HYATE:C administration.

| TREATMENT | | >25% | | >35% | |
|---|---|---|---|---|---|
| | | AUC | TIME(hr) | AUC | TIME(hr) |
| OBI-1 | | 1266.2 | 25.6 | 709.2 | 7.6 |
| | | 2219.3 | 27.2 | 1939.4 | 24.2 |
| | | 210.4 | 7.5 | 127.7 | 4.5 |
| | mean | 1232.0 | 20.1 | 925.4 | 12.1 |
| | Std Dev | 1004.9 | 10.9 | 925.0 | 10.6 |
| HYATE:C | | 387.7 | 9 | 302.7 | 9 |
| | | 236.4 | 9 | 179.9 | 9 |
| | | 193.4 | 8.9 | 101.4 | 6 |
| | mean | 272.5 | 9.0 | 194.7 | 8.0 |
| | Std Dev | 102.1 | 0.0 | 101.5 | 1.8 |

As shown in the above tables: (1) the AUC above 25% and 35% is approximately 5 times greater for OBI-1 than for HYATE:C (Table 9); (2) peak concentrations (Cmax) are 2-3 fold higher for OBI-1 than for Hyate:C (Table 8); (3) OBI-1 will achieve its peak concentration much more rapidly than will Hyate:C (see Tmax in Table 8, in which the Tmax for OBI-1 was approximately 0.6 hours compared to 1.5-2.0 hours for Hyate:C); and (4) the length of time FVIII will be in the therapeutic range after administration of OBI-1 at 100 U/kg is greater (1.5 to 2 fold) than for HYATE:C at 100 U/kg.

In summary, the data presented herein indicate that OBI-1, unit for unit, will achieve much more rapid, effective, and prolonged control of bleeding than HYATE:C in patients having fVIII deficiency.

Example 8

Clinical Results

Human patients diagnosed with congenital hemophilia A were screened for eligibility for an open-label study of OBI-1 efficacy based on criteria chosen to avoid potential complicating factors. Patients that qualified for treatment were those already known to have inhibitory antibodies to human factor VIII (hfVIII), and, with one exception, had <20 BU/ml plasma anti-porcine factor VIII (pfVIII). (For Bethesda assay, see Kasper, C. K. et al (1975) *Thromb. Diath. Haemorrh.* 34:869-872). All candidate patients were >12 years old, had no prior allergic reaction to OBI-1, no prior treatment with hfVII within 7 days of screening or OBI-1 treatment, no prior treatment with prothrombin complex concentrate within 7 days of screening or OBI-1 treatment, no prior treatment with human VII within 3 days of screening or OBI-1 treatment, no prior exposure to an unlicensed or investigational drug within 28 days of OBI-1 treatment, not pregnant nor breast feeding, nor, if a sexually active female capable of reproduction, taking contraceptive measures. Candidate patients were also excluded if they had significant liver or kidney disease.

The only bleeding episodes treated in the study were those deemed non-life threatening and non-limb threatening. Patients having an anti-porcine antibody titer of >0.8 BU/ml plasma were, with one exception noted below, given a Loading Dose immediately before administering the treatment dose, to neutralize the patient's anti-porcine fVIII antibodies, consistent with prior practice for administering HYATE:C. Following the established procedure for calculating a Loading Dose, the total Units of OBI-1=plasma volume (ml)×inhibitor titer (BU/ml), where plasma volume was calculated as blood volume×(1-hematocrit) and blood volume was calculated as body weight (kg)×80 ml/kg.

The standard treatment dose for each patient was 50 U/kg of patient weight of an OBI-1 solution of 500 U/ml. For example, a treatment dose for a 70 kg patient would therefore be 3500 total units in a volume of 7 ml. The treatment dose was infused at a rate of 1 ml (500 U) per minute, which would require, in the example, 7 minutes to administer the entire 3500 U to a 70 kg patient. By comparison HYATE:C at its available concentration of 26.75 U/ml would require 131.66 minutes, (2 hours 11.66 minutes) at 1 ml/min, to complete a treatment dose, for a 70 kg patient.

A Unit of Factor VIII is defined in the art as the coagulant activity present in 1 ml of normal human plasma. Normal plasmas display a range of individual variation. Therefore assays are carried out with pooled plasma samples, commercially available, as noted in Example 5. Commercial pooled plasma stocks can be standardized by assaying with a reference plasma from World Health Organization. Assay methods are well-known in the art, including one-stage and two-stage assays as described, for example by Barrowcliffe, T. W. et al (2002) Semin. Thromb. Hemost. 28:247-256, or in Example 5. A normal, non-hemophilic individual human is expected to have about 40 U/kg Factor VIII activity. Standard therapy for a bleeding episode using HYATE:C was infusion of 100 U/kg, followed by subsequent infusions of HYATE:C at 6-8 hour intervals until the bleeding was controlled, as determined by clinical observation. The protocol for the study reported herein established that each patient having a bleeding episode be given an initial treatment dose of 50 U/kg OBI-1. If needed, subsequent doses of 50 U/kg were to be administered at 6 hour intervals, for up to three doses, then, if needed, 100 U/kg for up to 6 total doses, and if needed, 150 U/kg for a seventh and eighth dose. Before treatment, a blood sample would be drawn to measure the patient's anti-porcine inhibitor titer, if any. Any patient having an inhibitor titer>0.8 BU/ml plasma was to be given a Loading Dose, as described above, followed by the protocol-established treatment dose.

Control of bleeding was defined in the protocol as a judgment by the patient and the investigator that no further factor replacement therapy was indicated for control of the bleeding episode.

The results to date (Table 10) indicate greater hemostatic efficacy of OBI-1 compared to HYATE:C.

TABLE 10

Summary of individual patient data

| Patient # | Site of bleed | anti OBI-1 titer at time of bleed | Last known anti OBI-1 titer | Treatment | OBI-1 U/Kg | Outcome |
|---|---|---|---|---|---|---|
| 1 | L ankle | 0.8 | 1.6 | LD + 3 TD | 74 50 50 50 | Controlled |
| 1 | R shoulder | 31.9 | <0.8 | 1 TD | 50 | Controlled |
| 2 | R elbow | 1.2 | <0.8 | 1 TD | 50 | Controlled |
| 2 | R elbow | ND | <0.8 | 1 TD | 50 | Controlled |
| 2 | Bleeding due to phimosis | 1.9 | 2.1 | LD + 1 TD | 109 50 | Controlled |
| 2 | Circumcision | ND | 1.9 | LD + 1 TD | 91 50 | Controlled |
| 2 | Loose sutures | 10.4 | 2.4* | LD + 1 TD | 91 50 | Controlled |
| 3 | L knee | 1.1 | 1.2 | LD + 1 TD | 65 50 | Controlled |
| 3 | Cut Lip** | ND | 11 | LD + 4 TD | 525 50 50 50 100 | Controlled |
| 4 | Wrist | Not available | 0.8 | 1 TD | 50 | Controlled |

LD—loading dose
ND—not done
TD—treatment dose
*-The site used a titer of 1.9 BU to calculate the LD
**-The bleeding stopped after the 3$^{rd}$ TD but the wound was still oozing and the investigator gave a 4$^{th}$ dose.

Of 10 bleeding episodes, 8 were controlled by a single Treatment Dose of OBI-1. None required more than 4 Treatment Doses. Direct comparisons with HYATE:C were not possible because it was withdrawn from the market in 2004. Nevertheless, the results are fully consistent with the bioavailability and pharmacokinetic data described in Examples 1-8.

Surprising results were obtained in cases where the standard Loading Dose was either omitted or reduced. In the case of Patient #1, a second bleeding episode occurred. Anti-OBI-1 titer measured at the time of the second bleed was unusually high, 31.9 BU/ml plasma. Nevertheless the bleeding episode was successfully controlled with a single 50 U/kg dose of OBI-1, without a prior Loading Dose to neutralize the antibody. In another instance, the fifth bleeding episode of patient #2, an anti OBI-1 titer of 10.4 BU was measured but the Loading Dose actually administered was calculated for a titer of 1.9 BU. The patient therefore received a Loading Dose only about ⅕ of that recommended by the protocol. Nevertheless the bleed was successfully controlled by a single Treatment Dose combined with the reduced Loading Dose. These data are contrary to the prior clinical experience with HYATE:C, where a Loading Dose was routinely administered. Even with the precaution of a loading dose, a HYATE:C patient was deemed likely to respond well only if the anti-porcine titer was <20.0 BU. The finding of hemostatic activity even in the presence of a high anti-OBI-1 titer is surprising in view of prior experience with HYATE:C, (Kernoff, P B A [1984] in *Factor VIII Inhibitors* [L. W. Hoyer, ed.] Alan R. Liss, New York, pp 207-224; Gatti, L. et al [1984] *Thromb. Haemost.* 51:379-384; Hay, C. et al [1995] in *Inhibitors to Coagulation Factors* [L. M. Aledort et al. eds.] Plenum Press, New York, pp.143-151; Hay, C R M [2000]*Haematologica* 85:21-24), but is at least consistent with other results on bioavailability and pharmacokinetics of OBI-1 described in Examples 1-7. The result is also consistent with the bioavailability data comparing OBI-1 and HYATE:C reported by Barrow R T, Lollar P (August, 2006) *J. Thromb. Haemost.* 2006. DOI: 10.1111/j.1538-7836.2006.02135.x suggesting that recombinant porcine fVIII could promote hemostasis on a time scale shorter than the 2 hours believed necessary for inactivation by antibodies.

In addition to improved bioavailability of OBI-1, physical availability at the locus of bleeding is significantly enhanced in relation to that of HYATE:C by its availability at higher concentration than was available with the latter product. Although the current protocol called for OBI-1 administration at a rate of 500 U/min (1 ml/min of a 500 U/ml solution), there is no inherent limitation to more rapid administration. Intravenous infusion can be carried out in ¹⁄₁₀ the time (1 ml/6 sec) without difficulty. Therefore enhanced physical availability of OBI-1 can be accomplished by administering the product at a rate of 5000 U/min. By providing a reconstituted OBI-1 solution of 1000 U/ml, double the concentration used in the protocol studies, a rate of administration of 10,000 U/min can be readily achieved. Since OBI-1 is far more pure than HYATE:C, administration of higher doses, e.g. up to 150 U/kg is feasible in cases where it might be deemed useful by a clinician.

Accordingly, OBI-1 can be administered to control bleeding in a patient having factor VIII deficiency without first administering a Loading Dose calculated to neutralize anti-porcine fVIII antibodies present in the patient's plasma. Also, more effective control of bleeding than was heretofore possible can be achieved by rapid intravenous infusion of OBI-1, at a rate of from 1000-10,000 U/min. Therefore the invention includes a method of administering a porcine partially B-domainless fVIII (OBI-1) to control a bleeding episode in a hemophilia A patient in need of such control comprising the steps of a) giving to the patient an intravenous dose of from 10-150 U/kg patient weight of OBI-1 at a rate of infusion of from 1,000-10,000 U/min, without administration of an antibody-neutralizing dose, whereby bleeding is controlled, or b) if bleeding is not controlled, giving subsequent doses as in step (a) at 4-12 hour intervals until bleeding is controlled.

Summary

The combined data of Examples 1-8 demonstrate the unexpected finding that OBI-1 behaves differently from HYATE:C in human and animal plasma. In particular, the studies described in Examples 6-8 employing human patients establish that recombinant porcine fVIII (OBI-1) indeed has far greater bioavailability than plasma-derived porcine fVIII (HYATE:C) in humans. This surprising result is precisely the opposite of what was seen with factor IX, where the plasma-derived concentrate had significantly greater recovery and bioavailability that the recombinant factor IX product (Ewenstein et al. supra). Furthermore, the greater bioavailability of OBI-1 compared to HYATE:C was also surprising, in light of the report by Kessler et al. (Haemophilia [2005] 11:84-91), in which B-domain deleted recombinant human fVIII (ReFacto®) was found to be bioequivalent to plasma-derived human fVIII (Hemofil® M) in various pharmacokinetic parameters measured in a randomized, three-way crossover study.

The results of all animal and human studies taken together make it possible to devise new protocols for administration of OBI-1, which differ substantially from conventional methods and dosage used for HYATE:C. One aspect of the invention provides a new dose regimen for OBI-1, whereby OBI-1 may be administered to a patient at as little as ⅙ the standard activity dose in units/kg recommended for HYATE:C. The recommended dose for HYATE:C was 100 U/kg of body wt in excess of the dose required to neutralize any patient antibody to porcine fVIII. The level of a patient's antibodies to porcine fVIII is different for each individual. The dose of OBI-1 required to neutralize the patient's antibodies can be estimated from measurement of antibody titer, using standard methods known in the art. Accordingly, for a given patient, one can administer OBI-1 in place of HYATE:C at a dose about as little as 10-20 U/kg of body wt in excess of the neutralizing dose. However, as shown in Example 8, control of bleeding in a patient with anti-OBI-1 inhibitor antibodies can be achieved using OBI-1 at one-half the standard HYATE:C dose without prior antibody neutralization. An effective dose of OBI-1 can be administered in a fraction of the volume of solution required for administering a dose of HYATE:C, not only because OBI-1 can be prepared in more concentrated form, but also because a smaller dose of OBI-1 can yield a recovery of activity comparable to a 2 to 6 fold higher dose of HYATE:C. Alternatively, if 100 U/kg of 150 U/kg of OBI-1 is employed as a dose, patients can be successfully managed with much fewer infusions required to halt a bleed or much longer intervals between injections of OBI-1. For example, where HYATE:C, required a median of eight infusions to halt a single bleeding episode over a two day period, OBI-1 can require only 1-4 such infusions, a dramatic advance in patient treatment. In addition, acute bleeding episodes can be treated with fewer and smaller doses of OBI-1, compared to 8 doses over 2 days, the median dosage of HYATE:C reported in its package insert. The OBI-1 dosage can bring about more rapid control of bleeding and therefore is likely both more effective and safer than HYATE:C. It is also advantageous for patient comfort and quality of life, as well as providing a reduced risk of infection and of side effects from contaminants. Therapeutic levels of fVIII can be achieved more rapidly by infusing the concentrated OBI-1 product. Another aspect of the invention provides a therapeutic protocol that includes a step of measuring OBI-1 recovery as part of the process for establishing an optimal dose in an individual patient. OBI-1 recovery can be measured essentially as described in Example 5, by adding a measured amount of OBI-1 activity to a sample of a patient's plasma, then measuring the activity recovered from the sample after a short time interval. A series of such tests can establish an OBI-1 dose suitable for each patient. Alternatively, individual recovery data can be measured directly in a patient. The methods of the present invention should also result in cost savings for treatment.

The foregoing exemplary descriptions and the illustrative preferred embodiments of the present invention have been explained in the drawings and described in detail, with varying modifications and alternative embodiments being taught. While the invention has been so shown, described and illustrated, it should be understood by those skilled in the art that equivalent changes in form and detail may be made therein without departing from the true spirit and scope of the invention, and that the scope of the invention is to be limited only to the claims except as precluded by the prior art. Moreover, the invention as disclosed herein, may be suitably practiced in the absence of the specific elements that are disclosed herein.

Whenever a range is given in the specification, for example, a temperature range, a time range, or a composition or concentration range, all intermediate ranges and subranges, as well as all individual values included in the ranges given are intended to be included in the disclosure.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when a compound is claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising," "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that starting materials, reagents, solid substrates, synthetic methods, purification methods, and analytical methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

All references cited herein are hereby incorporated by reference to the extent that there is no inconsistency with the disclosure of this specification. Some references provided herein are incorporated by reference to provide details concerning sources of starting materials, additional starting materials, additional reagents, additional methods of synthesis, additional methods of analysis and additional uses of the invention.

We claim:

1. A method of reducing blood clotting time in a patient having factor VIII deficiency, comprising administering a composition comprising a porcine partially B-domainless factor VIII (OBI-1) and a physiologically acceptable carrier to the patient in need thereof in an amount sufficient to reduce the patient's blood clotting time to a desired value wherein the amount of OBI-1 sufficient to reduce the patient's blood clotting time is ½ to 1/10 of the amount of plasma-derived porcine factor VIII sufficient to achieve the same reduction of blood clotting time obtained upon administering the partially B-domainless porcine fVIII (OBI-1), and wherein said OBI-1 is the expression product of SEQ ID NO:1.

2. The method of claim 1, wherein the plasma-derived porcine fVIII is HYATE:C.

3. The method of claim 1, wherein a first administration of an amount of porcine partially B-domainless fVIII (OBI-1) that reduces the patient's blood clotting time to a desired value is followed by a second administration of an amount of porcine partially B-domainless fVIII (OBI-1) that reduces the patient blood clotting time to the desired value, the patient's blood clotting time remaining reduced at or near said desired value during such time interval, and said time interval being at least 2-fold greater than the corresponding time interval within which said desired value can be maintained by administration of the same dose of porcine plasma-derived fVIII, and wherein said OBI-1 is the expression product of SEQ ID NO:1.

4. The method of claim 3, wherein the porcine plasma-derived fVIII is HYATE:C.

* * * * *

SEQUENCE LISTING

<160> NUMBER OF SEQ ID NOS: 2

<210> SEQ ID NO 1
<211> LENGTH: 4404
<212> TYPE: DNA
<213> ORGANISM: Artificial
<220> FEATURE:
<223> OTHER INFORMATION: Synthetic construct: porcine factor VIII
coding sequence engineered to remove most of B domain from encoded
product.
<220> FEATURE:
<221> NAME/KEY: CDS
<222> LOCATION: (1)..(4401)
<220> FEATURE:
<221> NAME/KEY: mat_peptide
<222> LOCATION: (58)..(4401)

<400> SEQUENCE: 1

```
atg cag cta gag ctc tcc acc tgt gtc ttt ctg tgt ctc ttg cca ctc      48
Met Gln Leu Glu Leu Ser Thr Cys Val Phe Leu Cys Leu Leu Pro Leu
            -15                 -10                  -5 ggc ttt agt gcc atc agg aga tac tac ctg ggc gca gtg gaa ctg tcc      96
Gly Phe Ser Ala Ile Arg Arg Tyr Tyr Leu Gly Ala Val Glu Leu Ser
     -1   1               5                   10 tgg gac tac cgg caa agt gaa ctc ctc cgt gag ctg cac gtg gac acc     144
Trp Asp Tyr Arg Gln Ser Glu Leu Leu Arg Glu Leu His Val Asp Thr
 15                  20                  25 aga ttt cct gct aca gcg cca gga gct ctt ccg ttg ggc ccg tca gtc     192
Arg Phe Pro Ala Thr Ala Pro Gly Ala Leu Pro Leu Gly Pro Ser Val
 30              35                  40                  45 ctg tac aaa aag act gtg ttc gta gag ttc acg gat caa ctt ttc agc     240
Leu Tyr Lys Lys Thr Val Phe Val Glu Phe Thr Asp Gln Leu Phe Ser
                 50                  55                  60 gtt gcc agg ccc agg cca cca tgg atg ggt ctg ctg ggt cct acc atc     288
Val Ala Arg Pro Arg Pro Pro Trp Met Gly Leu Leu Gly Pro Thr Ile
             65                  70                  75 cag gct gag gtt tac gac acg gtg gtc gtt acc ctg aag aac atg gct     336
Gln Ala Glu Val Tyr Asp Thr Val Val Val Thr Leu Lys Asn Met Ala
         80                  85                  90 tct cat ccc gtt agt ctt cac gct gtc ggc gtc tcc ttc tgg aaa tct     384
Ser His Pro Val Ser Leu His Ala Val Gly Val Ser Phe Trp Lys Ser
 95                 100                 105 tcc gaa ggc gct gaa tat gag gat cac acc agc caa agg gag aag gaa     432
Ser Glu Gly Ala Glu Tyr Glu Asp His Thr Ser Gln Arg Glu Lys Glu
110                 115                 120                 125 gac gat aaa gtc ctt ccc ggt aaa agc caa acc tac gtc tgg cag gtc     480
Asp Asp Lys Val Leu Pro Gly Lys Ser Gln Thr Tyr Val Trp Gln Val
                130                 135                 140 ctg aaa gaa aat ggt cca aca gcc tct gac cca cca tgt ctt acc tac     528
Leu Lys Glu Asn Gly Pro Thr Ala Ser Asp Pro Pro Cys Leu Thr Tyr
            145                 150                 155 tca tac ctg tct cac gtg gac ctg gtg aaa gac ctg aat tcg ggc ctc     576
Ser Tyr Leu Ser His Val Asp Leu Val Lys Asp Leu Asn Ser Gly Leu
        160                 165                 170 att gga gcc ctg ctg gtt tgt aga gaa ggg agt ctg acc aga gaa agg     624
Ile Gly Ala Leu Leu Val Cys Arg Glu Gly Ser Leu Thr Arg Glu Arg
    175                 180                 185 acc cag aac ctg cac gaa ttt gta cta ctt ttt gct gtc ttt gat gaa     672
Thr Gln Asn Leu His Glu Phe Val Leu Leu Phe Ala Val Phe Asp Glu
190                 195                 200                 205 ggg aaa agt tgg cac tca gca aga aat gac tcc tgg aca cgg gcc atg     720
Gly Lys Ser Trp His Ser Ala Arg Asn Asp Ser Trp Thr Arg Ala Met
```

-continued

|     |     |     | 210 |     |     |     | 215 |     |     |     | 220 |     |     |     |      |
|---|---|---|---|---|---|---|---|---|---|---|---|---|---|---|---|
| gat | ccc | gca | cct | gcc | agg | gcc | cag | cct | gca | atg | cac | aca | gtc | aat | ggc | 768
| Asp | Pro | Ala | Pro | Ala | Arg | Ala | Gln | Pro | Ala | Met | His | Thr | Val | Asn | Gly |
|     |     |     | 225 |     |     |     | 230 |     |     |     | 235 |     |     |     |      |

```
gat ccc gca cct gcc agg gcc cag cct gca atg cac aca gtc aat ggc      768
Asp Pro Ala Pro Ala Arg Ala Gln Pro Ala Met His Thr Val Asn Gly
            225                 230                 235 tat gtc aac agg tct ctg cca ggt ctg atc gga tgt cat aag aaa tca      816
Tyr Val Asn Arg Ser Leu Pro Gly Leu Ile Gly Cys His Lys Lys Ser
            240                 245                 250 gtc tac tgg cac gtg att gga atg ggc acc agc ccg gaa gtg cac tcc      864
Val Tyr Trp His Val Ile Gly Met Gly Thr Ser Pro Glu Val His Ser
            255                 260                 265 att ttt ctt gaa ggc cac acg ttt ctc gtg agg cac cat cgc cag gct      912
Ile Phe Leu Glu Gly His Thr Phe Leu Val Arg His His Arg Gln Ala
270                 275                 280                 285 tcc ttg gag atc tcg cca cta act ttc ctc act gct cag aca ttc ctg      960
Ser Leu Glu Ile Ser Pro Leu Thr Phe Leu Thr Ala Gln Thr Phe Leu
            290                 295                 300 atg gac ctt ggc cag ttc cta ctg ttt tgt cat atc tct tcc cac cac     1008
Met Asp Leu Gly Gln Phe Leu Leu Phe Cys His Ile Ser Ser His His
            305                 310                 315 cat ggt ggc atg gag gct cac gtc aga gta gaa agc tgc gcc gag gag     1056
His Gly Gly Met Glu Ala His Val Arg Val Glu Ser Cys Ala Glu Glu
            320                 325                 330 ccc cag ctg cgg agg aaa gct gat gaa gag gaa gat tat gat gac aat     1104
Pro Gln Leu Arg Arg Lys Ala Asp Glu Glu Glu Asp Tyr Asp Asp Asn
            335                 340                 345 ttg tac gac tcg gac atg gac gtg gtc cgg ctc gat ggt gac gac gtg     1152
Leu Tyr Asp Ser Asp Met Asp Val Val Arg Leu Asp Gly Asp Asp Val
350                 355                 360                 365 tct ccc ttt atc caa atc cgc tcg gtt gcc aag aag cat ccc aaa acc     1200
Ser Pro Phe Ile Gln Ile Arg Ser Val Ala Lys Lys His Pro Lys Thr
            370                 375                 380 tgg gtg cac tac atc tct gca gag gag gag gac tgg gac tac gcc ccc     1248
Trp Val His Tyr Ile Ser Ala Glu Glu Glu Asp Trp Asp Tyr Ala Pro
            385                 390                 395 gcg gtc ccc agc ccc agt gac aga agt tat aaa agt ctc tac ttg aac     1296
Ala Val Pro Ser Pro Ser Asp Arg Ser Tyr Lys Ser Leu Tyr Leu Asn
            400                 405                 410 agt ggt cct cag cga att ggt agg aaa tac aaa aaa gct cga ttc gtc     1344
Ser Gly Pro Gln Arg Ile Gly Arg Lys Tyr Lys Lys Ala Arg Phe Val
            415                 420                 425 gct tac acg gat gta aca ttt aag act cgt aaa gct att ccg tat gaa     1392
Ala Tyr Thr Asp Val Thr Phe Lys Thr Arg Lys Ala Ile Pro Tyr Glu
430                 435                 440                 445 tca gga atc ctg gga cct tta ctt tat gga gaa gtt gga gac aca ctt     1440
Ser Gly Ile Leu Gly Pro Leu Leu Tyr Gly Glu Val Gly Asp Thr Leu
            450                 455                 460 ttg att ata ttt aag aat aaa gcg agc cga cca tat aac atc tac cct     1488
Leu Ile Ile Phe Lys Asn Lys Ala Ser Arg Pro Tyr Asn Ile Tyr Pro
            465                 470                 475 cat gga atc act gat gtc agc gct ttg cac cca ggg aga ctt cta aaa     1536
His Gly Ile Thr Asp Val Ser Ala Leu His Pro Gly Arg Leu Leu Lys
            480                 485                 490 ggt tgg aaa cat ttg aaa gac atg cca att ctg cca gga gag act ttc     1584
Gly Trp Lys His Leu Lys Asp Met Pro Ile Leu Pro Gly Glu Thr Phe
            495                 500                 505 aag tat aaa tgg aca gtg act gtg gaa gat ggg cca acc aag tcc gat     1632
Lys Tyr Lys Trp Thr Val Thr Val Glu Asp Gly Pro Thr Lys Ser Asp
510                 515                 520                 525 cct cgg tgc ctg acc cgc tac tac tcg agc tcc att aat cta gag aaa     1680
Pro Arg Cys Leu Thr Arg Tyr Tyr Ser Ser Ser Ile Asn Leu Glu Lys
```

```
                530                 535                 540
gat ctg gct tcg gga ctc att ggc cct ctc ctc atc tgc tac aaa gaa        1728
Asp Leu Ala Ser Gly Leu Ile Gly Pro Leu Leu Ile Cys Tyr Lys Glu
            545                 550                 555 tct gta gac caa aga gga aac cag atg atg tca gac aag aga aac gtc        1776
Ser Val Asp Gln Arg Gly Asn Gln Met Met Ser Asp Lys Arg Asn Val
            560                 565                 570 atc ctg ttt tct gta ttc gat gag aat caa agc tgg tac ctc gca gag        1824
Ile Leu Phe Ser Val Phe Asp Glu Asn Gln Ser Trp Tyr Leu Ala Glu
            575                 580                 585 aat att cag cgc ttc ctc ccc aat ccg gat gga tta cag ccc cag gat        1872
Asn Ile Gln Arg Phe Leu Pro Asn Pro Asp Gly Leu Gln Pro Gln Asp
590                 595                 600                 605 cca gag ttc caa gct tct aac atc atg cac agc atc aat ggc tat gtt        1920
Pro Glu Phe Gln Ala Ser Asn Ile Met His Ser Ile Asn Gly Tyr Val
                610                 615                 620 ttt gat agc ttg cag ctg tcg gtt tgt ttg cac gag gtg gca tac tgg        1968
Phe Asp Ser Leu Gln Leu Ser Val Cys Leu His Glu Val Ala Tyr Trp
            625                 630                 635 tac att cta agt gtt gga gca cag acg gac ttc ctc tcc gtc ttc ttc        2016
Tyr Ile Leu Ser Val Gly Ala Gln Thr Asp Phe Leu Ser Val Phe Phe
            640                 645                 650 tct ggc tac acc ttc aaa cac aaa atg gtc tat gaa gac aca ctc acc        2064
Ser Gly Tyr Thr Phe Lys His Lys Met Val Tyr Glu Asp Thr Leu Thr
            655                 660                 665 ctg ttc ccc ttc tca gga gaa acg gtc ttc atg tca atg gaa aac cca        2112
Leu Phe Pro Phe Ser Gly Glu Thr Val Phe Met Ser Met Glu Asn Pro
670                 675                 680                 685 ggt ctc tgg gtc ctt ggg tgc cac aac tca gac ttg cgg aac aga ggg        2160
Gly Leu Trp Val Leu Gly Cys His Asn Ser Asp Leu Arg Asn Arg Gly
                690                 695                 700 atg aca gcc tta ctg aag gtg tat agt tgt gac agg gac att ggt gat        2208
Met Thr Ala Leu Leu Lys Val Tyr Ser Cys Asp Arg Asp Ile Gly Asp
            705                 710                 715 tat tat gac aac act tat gaa gat att cca ggc ttc ttg ctg agt gga        2256
Tyr Tyr Asp Asn Thr Tyr Glu Asp Ile Pro Gly Phe Leu Leu Ser Gly
            720                 725                 730 aag aat gtc att gaa cct agg agc ttt gcc cag aat tca aga ccc cct        2304
Lys Asn Val Ile Glu Pro Arg Ser Phe Ala Gln Asn Ser Arg Pro Pro
735                 740                 745 agt gcg agc gct cca aag cct ccg gtc ctg cga cgg cat cag agg gac        2352
Ser Ala Ser Ala Pro Lys Pro Pro Val Leu Arg Arg His Gln Arg Asp
750                 755                 760                 765 ata agc ctt cct act ttt cag ccg gag gaa gac aaa atg gac tat gat        2400
Ile Ser Leu Pro Thr Phe Gln Pro Glu Glu Asp Lys Met Asp Tyr Asp
                770                 775                 780 gat atc ttc tca act gaa acg aag gga gaa gat ttt gac att tac ggt        2448
Asp Ile Phe Ser Thr Glu Thr Lys Gly Glu Asp Phe Asp Ile Tyr Gly
            785                 790                 795 gag gat gaa aat cag gac cct cgc agc ttt cag aag aga acc cga cac        2496
Glu Asp Glu Asn Gln Asp Pro Arg Ser Phe Gln Lys Arg Thr Arg His
            800                 805                 810 tat ttc att gct gcg gtg gag cag ctc tgg gat tac ggg atg agc gaa        2544
Tyr Phe Ile Ala Ala Val Glu Gln Leu Trp Asp Tyr Gly Met Ser Glu
            815                 820                 825 tcc ccc cgg gcg cta aga aac agg gct cag aac gga gag gtg cct cgg        2592
Ser Pro Arg Ala Leu Arg Asn Arg Ala Gln Asn Gly Glu Val Pro Arg
830                 835                 840                 845 ttc aag aag gtg gtc ttc cgg gaa ttt gct gac ggc tcc ttc acg cag        2640
Phe Lys Lys Val Val Phe Arg Glu Phe Ala Asp Gly Ser Phe Thr Gln
```

|  |  |
|---|---|
| ccg tcg tac cgc ggg gaa ctc aac aaa cac ttg ggg ctc ttg gga ccc<br>Pro Ser Tyr Arg Gly Glu Leu Asn Lys His Leu Gly Leu Leu Gly Pro<br>          865                        870                          875 | 2688 |
| tac atc aga gcg aaa gtt gaa gac aac atc atg gta act ttc aaa aac<br>Tyr Ile Arg Ala Glu Val Glu Asp Asn Ile Met Val Thr Phe Lys Asn<br>          880                        885                        890 | 2736 |
| cag gcg tct cgt ccc tat tcc ttc tac tcg agc ctt att tct tat ccg<br>Gln Ala Ser Arg Pro Tyr Ser Phe Tyr Ser Ser Leu Ile Ser Tyr Pro<br>   895                        900                        905 | 2784 |
| gat gat cag gag caa ggg gca gaa cct cga cac aac ttc gtc cag cca<br>Asp Asp Gln Glu Gln Gly Ala Glu Pro Arg His Asn Phe Val Gln Pro<br>910                        915                        920                        925 | 2832 |
| aat gaa acc aga act tac ttt tgg aaa gtg cag cat cac atg gca ccc<br>Asn Glu Thr Arg Thr Tyr Phe Trp Lys Val Gln His His Met Ala Pro<br>          930                        935                        940 | 2880 |
| aca gaa gac gag ttt gac tgc aaa gcc tgg gcc tac ttt tct gat gtt<br>Thr Glu Asp Glu Phe Asp Cys Lys Ala Trp Ala Tyr Phe Ser Asp Val<br>   945                        950                        955 | 2928 |
| gac ctg gaa aaa gat gtg cac tca ggc ttg atc ggc ccc ctt ctg atc<br>Asp Leu Glu Lys Asp Val His Ser Gly Leu Ile Gly Pro Leu Leu Ile<br>960                        965                        970 | 2976 |
| tgc cgc gcc aac acc ctg aac gct gct cac ggt aga caa gtg acc gtg<br>Cys Arg Ala Asn Thr Leu Asn Ala Ala His Gly Arg Gln Val Thr Val<br>   975                        980                        985 | 3024 |
| caa gaa ttt gct ctg ttt ttc act att ttt gat gag aca aag agc tgg<br>Gln Glu Phe Ala Leu Phe Phe Thr Ile Phe Asp Glu Thr Lys Ser Trp<br>990                        995                      1000                  1005 | 3072 |
| tac ttc act gaa aat gtg gaa agg aac tgc cgg gcc ccc tgc cat<br>Tyr Phe Thr Glu Asn Val Glu Arg Asn Cys Arg Ala Pro Cys His<br>               1010                      1015                      1020 | 3117 |
| ctg cag atg gag gac ccc act ctg aaa gaa aac tat cgc ttc cat<br>Leu Gln Met Glu Asp Pro Thr Leu Lys Glu Asn Tyr Arg Phe His<br>               1025                      1030                      1035 | 3162 |
| gca atc aat ggc tat gtg atg gat aca ctc cct ggc tta gta atg<br>Ala Ile Asn Gly Tyr Val Met Asp Thr Leu Pro Gly Leu Val Met<br>               1040                      1045                      1050 | 3207 |
| gct cag aat caa agg atc cga tgg tat ctg ctc agc atg ggc agc<br>Ala Gln Asn Gln Arg Ile Arg Trp Tyr Leu Leu Ser Met Gly Ser<br>               1055                      1060                      1065 | 3252 |
| aat gaa aat atc cat tcg att cat ttt agc gga cac gtg ttc agt<br>Asn Glu Asn Ile His Ser Ile His Phe Ser Gly His Val Phe Ser<br>               1070                      1075                      1080 | 3297 |
| gta cgg aaa aag gag gag tat aaa atg gcc gtg tac aat ctc tat<br>Val Arg Lys Lys Glu Glu Tyr Lys Met Ala Val Tyr Asn Leu Tyr<br>               1085                      1090                      1095 | 3342 |
| ccg ggt gtc ttt gag aca gtg gaa atg cta ccg tcc aaa gtt gga<br>Pro Gly Val Phe Glu Thr Val Glu Met Leu Pro Ser Lys Val Gly<br>               1100                      1105                      1110 | 3387 |
| att tgg cga ata gaa tgc ctg att ggc gag cac ctg caa gct ggg<br>Ile Trp Arg Ile Glu Cys Leu Ile Gly Glu His Leu Gln Ala Gly<br>               1115                      1120                      1125 | 3432 |
| atg agc acg act ttc ctg gtg tac agc aag gag tgt cag gct cca<br>Met Ser Thr Thr Phe Leu Val Tyr Ser Lys Glu Cys Gln Ala Pro<br>               1130                      1135                      1140 | 3477 |
| ctg gga atg gct tct gga cgc att aga gat ttt cag atc aca gct<br>Leu Gly Met Ala Ser Gly Arg Ile Arg Asp Phe Gln Ile Thr Ala<br>               1145                      1150                      1155 | 3522 |
| tca gga cag tat gga cag tgg gcc cca aag ctg gcc aga ctt cat<br>Ser Gly Gln Tyr Gly Gln Trp Ala Pro Lys Leu Ala Arg Leu His | 3567 |

|  |  |  |  |  |  |  |  |  |  |  |  |  |  |  | |
|---|---|---|---|---|---|---|---|---|---|---|---|---|---|---|---|
|  |  | 1160 |  |  |  | 1165 |  |  |  | 1170 |  |  |  |  | |
| tat | tcc | gga | tca | atc | aat | gcc | tgg | agc | acc | aag | gat | ccc | cac | tcc | 3612 |
| Tyr | Ser | Gly | Ser | Ile | Asn | Ala | Trp | Ser | Thr | Lys | Asp | Pro | His | Ser | |
|  |  |  |  | 1175 |  |  |  |  | 1180 |  |  |  |  | 1185 | |
| tgg | atc | aag | gtg | gat | ctg | ttg | gca | cca | atg | atc | att | cac | ggc | atc | 3657 |
| Trp | Ile | Lys | Val | Asp | Leu | Leu | Ala | Pro | Met | Ile | Ile | His | Gly | Ile | |
|  |  |  |  | 1190 |  |  |  |  | 1195 |  |  |  |  | 1200 | |
| atg | acc | cag | ggt | gcc | cgt | cag | aag | ttt | tcc | agc | ctc | tac | atc | tcc | 3702 |
| Met | Thr | Gln | Gly | Ala | Arg | Gln | Lys | Phe | Ser | Ser | Leu | Tyr | Ile | Ser | |
|  |  |  |  | 1205 |  |  |  |  | 1210 |  |  |  |  | 1215 | |
| cag | ttt | atc | atc | atg | tac | agt | ctt | gac | ggg | agg | aac | tgg | cag | agt | 3747 |
| Gln | Phe | Ile | Ile | Met | Tyr | Ser | Leu | Asp | Gly | Arg | Asn | Trp | Gln | Ser | |
|  |  |  |  | 1220 |  |  |  |  | 1225 |  |  |  |  | 1230 | |
| tac | cga | ggg | aat | tcc | acg | ggc | acc | tta | atg | gtc | ttc | ttt | ggc | aat | 3792 |
| Tyr | Arg | Gly | Asn | Ser | Thr | Gly | Thr | Leu | Met | Val | Phe | Phe | Gly | Asn | |
|  |  |  |  | 1235 |  |  |  |  | 1240 |  |  |  |  | 1245 | |
| gtg | gac | gca | tct | ggg | att | aaa | cac | aat | att | ttt | aac | cct | ccg | att | 3837 |
| Val | Asp | Ala | Ser | Gly | Ile | Lys | His | Asn | Ile | Phe | Asn | Pro | Pro | Ile | |
|  |  |  |  | 1250 |  |  |  |  | 1255 |  |  |  |  | 1260 | |
| gtg | gct | cgg | tac | atc | cgt | ttg | cac | cca | aca | cat | tac | agc | atc | cgc | 3882 |
| Val | Ala | Arg | Tyr | Ile | Arg | Leu | His | Pro | Thr | His | Tyr | Ser | Ile | Arg | |
|  |  |  |  | 1265 |  |  |  |  | 1270 |  |  |  |  | 1275 | |
| agc | act | ctt | cgc | atg | gag | ttg | atg | ggc | tgt | gat | tta | aac | agt | tgc | 3927 |
| Ser | Thr | Leu | Arg | Met | Glu | Leu | Met | Gly | Cys | Asp | Leu | Asn | Ser | Cys | |
|  |  |  |  | 1280 |  |  |  |  | 1285 |  |  |  |  | 1290 | |
| agc | atg | ccc | ctg | gga | atg | cag | aat | aaa | gcg | ata | tca | gac | tca | cag | 3972 |
| Ser | Met | Pro | Leu | Gly | Met | Gln | Asn | Lys | Ala | Ile | Ser | Asp | Ser | Gln | |
|  |  |  |  | 1295 |  |  |  |  | 1300 |  |  |  |  | 1305 | |
| atc | acg | gcc | tcc | tcc | cac | cta | agc | aat | ata | ttt | gcc | acc | tgg | tct | 4017 |
| Ile | Thr | Ala | Ser | Ser | His | Leu | Ser | Asn | Ile | Phe | Ala | Thr | Trp | Ser | |
|  |  |  |  | 1310 |  |  |  |  | 1315 |  |  |  |  | 1320 | |
| cct | tca | caa | gcc | cga | ctt | cac | ctc | cag | ggg | cgg | acg | aat | gcc | tgg | 4062 |
| Pro | Ser | Gln | Ala | Arg | Leu | His | Leu | Gln | Gly | Arg | Thr | Asn | Ala | Trp | |
|  |  |  |  | 1325 |  |  |  |  | 1330 |  |  |  |  | 1335 | |
| cga | ccc | cgg | gtg | agc | agc | gca | gag | gag | tgg | ctg | cag | gtg | gac | ctg | 4107 |
| Arg | Pro | Arg | Val | Ser | Ser | Ala | Glu | Glu | Trp | Leu | Gln | Val | Asp | Leu | |
|  |  |  |  | 1340 |  |  |  |  | 1345 |  |  |  |  | 1350 | |
| cag | aag | acg | gtg | aag | gtc | aca | ggc | atc | acc | acc | cag | ggc | gtg | aag | 4152 |
| Gln | Lys | Thr | Val | Lys | Val | Thr | Gly | Ile | Thr | Thr | Gln | Gly | Val | Lys | |
|  |  |  |  | 1355 |  |  |  |  | 1360 |  |  |  |  | 1365 | |
| tcc | ctg | ctc | agc | agc | atg | tat | gtg | aag | gag | ttc | ctc | gtg | tcc | agt | 4197 |
| Ser | Leu | Leu | Ser | Ser | Met | Tyr | Val | Lys | Glu | Phe | Leu | Val | Ser | Ser | |
|  |  |  |  | 1370 |  |  |  |  | 1375 |  |  |  |  | 1380 | |
| agt | cag | gac | ggc | cgc | cgc | tgg | acc | ctg | ttt | ctt | cag | gac | ggc | cac | 4242 |
| Ser | Gln | Asp | Gly | Arg | Arg | Trp | Thr | Leu | Phe | Leu | Gln | Asp | Gly | His | |
|  |  |  |  | 1385 |  |  |  |  | 1390 |  |  |  |  | 1395 | |
| acg | aag | gtt | ttt | cag | ggc | aat | cag | gac | tcc | tcc | acc | ccc | gtg | gtg | 4287 |
| Thr | Lys | Val | Phe | Gln | Gly | Asn | Gln | Asp | Ser | Ser | Thr | Pro | Val | Val | |
|  |  |  |  | 1400 |  |  |  |  | 1405 |  |  |  |  | 1410 | |
| aac | gct | ctg | gac | ccc | ccg | ctg | ttc | acg | cgc | tac | ctg | agg | atc | cac | 4332 |
| Asn | Ala | Leu | Asp | Pro | Pro | Leu | Phe | Thr | Arg | Tyr | Leu | Arg | Ile | His | |
|  |  |  |  | 1415 |  |  |  |  | 1420 |  |  |  |  | 1425 | |
| ccc | acg | agc | tgg | gcg | cag | cac | atc | gcc | ctg | agg | ctc | gag | gtt | cta | 4377 |
| Pro | Thr | Ser | Trp | Ala | Gln | His | Ile | Ala | Leu | Arg | Leu | Glu | Val | Leu | |
|  |  |  |  | 1430 |  |  |  |  | 1435 |  |  |  |  | 1440 | |
| gga | tgt | gag | gca | cag | gat | ctc | tac | tga |  |  |  |  |  |  | 4404 |
| Gly | Cys | Glu | Ala | Gln | Asp | Leu | Tyr |  |  |  |  |  |  |  | |
|  |  |  |  | 1445 |  |  |  |  |  |  |  |  |  |  | |

<210> SEQ ID NO 2

-continued

```
<211> LENGTH: 1467
<212> TYPE: PRT
<213> ORGANISM: Artificial
<220> FEATURE:
<223> OTHER INFORMATION: Synthetic Construct

<400> SEQUENCE: 2

Met Gln Leu Glu Leu Ser Thr Cys Val Phe Leu Cys Leu Leu Pro Leu
                -15                 -10                  -5

Gly Phe Ser Ala Ile Arg Arg Tyr Tyr Leu Gly Ala Val Glu Leu Ser
            -1  1               5                  10

Trp Asp Tyr Arg Gln Ser Glu Leu Leu Arg Glu Leu His Val Asp Thr
     15              20                  25

Arg Phe Pro Ala Thr Ala Pro Gly Ala Leu Pro Leu Gly Pro Ser Val
 30              35                  40                  45

Leu Tyr Lys Lys Thr Val Phe Val Glu Phe Thr Asp Gln Leu Phe Ser
             50                  55                  60

Val Ala Arg Pro Arg Pro Pro Trp Met Gly Leu Leu Gly Pro Thr Ile
             65                  70                  75

Gln Ala Glu Val Tyr Asp Thr Val Val Thr Leu Lys Asn Met Ala
 80                  85                  90

Ser His Pro Val Ser Leu His Ala Val Gly Val Ser Phe Trp Lys Ser
 95                 100                 105

Ser Glu Gly Ala Glu Tyr Glu Asp His Thr Ser Gln Arg Glu Lys Glu
110                 115                 120                 125

Asp Asp Lys Val Leu Pro Gly Lys Ser Gln Thr Tyr Val Trp Gln Val
                130                 135                 140

Leu Lys Glu Asn Gly Pro Thr Ala Ser Asp Pro Pro Cys Leu Thr Tyr
            145                 150                 155

Ser Tyr Leu Ser His Val Asp Leu Val Lys Asp Leu Asn Ser Gly Leu
        160                 165                 170

Ile Gly Ala Leu Leu Val Cys Arg Glu Gly Ser Leu Thr Arg Glu Arg
    175                 180                 185

Thr Gln Asn Leu His Glu Phe Val Leu Leu Phe Ala Val Phe Asp Glu
190                 195                 200                 205

Gly Lys Ser Trp His Ser Ala Arg Asn Asp Ser Trp Thr Arg Ala Met
                210                 215                 220

Asp Pro Ala Pro Ala Arg Ala Gln Pro Ala Met His Thr Val Asn Gly
                225                 230                 235

Tyr Val Asn Arg Ser Leu Pro Gly Leu Ile Gly Cys His Lys Lys Ser
            240                 245                 250

Val Tyr Trp His Val Ile Gly Met Gly Thr Ser Pro Glu Val His Ser
        255                 260                 265

Ile Phe Leu Glu Gly His Thr Phe Leu Val Arg His His Arg Gln Ala
270                 275                 280                 285

Ser Leu Glu Ile Ser Pro Leu Thr Phe Leu Thr Ala Gln Thr Phe Leu
                290                 295                 300

Met Asp Leu Gly Gln Phe Leu Leu Phe Cys His Ile Ser Ser His His
            305                 310                 315

His Gly Gly Met Glu Ala His Val Arg Val Glu Ser Cys Ala Glu Glu
        320                 325                 330

Pro Gln Leu Arg Arg Lys Ala Asp Glu Glu Asp Tyr Asp Asp Asn
            335                 340                 345

Leu Tyr Asp Ser Asp Met Asp Val Val Arg Leu Asp Gly Asp Asp Val
350                 355                 360                 365
```

```
Ser Pro Phe Ile Gln Ile Arg Ser Val Ala Lys Lys His Pro Lys Thr
                370                 375                 380

Trp Val His Tyr Ile Ser Ala Glu Glu Asp Trp Asp Tyr Ala Pro
            385                 390                 395

Ala Val Pro Ser Pro Ser Asp Arg Ser Tyr Lys Ser Leu Tyr Leu Asn
            400                 405                 410

Ser Gly Pro Gln Arg Ile Gly Arg Lys Tyr Lys Ala Arg Phe Val
    415                 420                 425

Ala Tyr Thr Asp Val Thr Phe Lys Thr Arg Lys Ala Ile Pro Tyr Glu
430                 435                 440                 445

Ser Gly Ile Leu Gly Pro Leu Leu Tyr Gly Glu Val Gly Asp Thr Leu
                450                 455                 460

Leu Ile Ile Phe Lys Asn Lys Ala Ser Arg Pro Tyr Asn Ile Tyr Pro
            465                 470                 475

His Gly Ile Thr Asp Val Ser Ala Leu His Pro Gly Arg Leu Leu Lys
            480                 485                 490

Gly Trp Lys His Leu Lys Asp Met Pro Ile Leu Pro Gly Glu Thr Phe
    495                 500                 505

Lys Tyr Lys Trp Thr Val Thr Val Glu Asp Gly Pro Thr Lys Ser Asp
510                 515                 520                 525

Pro Arg Cys Leu Thr Arg Tyr Tyr Ser Ser Ile Asn Leu Glu Lys
                530                 535                 540

Asp Leu Ala Ser Gly Leu Ile Gly Pro Leu Leu Ile Cys Tyr Lys Glu
            545                 550                 555

Ser Val Asp Gln Arg Gly Asn Gln Met Met Ser Asp Lys Arg Asn Val
    560                 565                 570

Ile Leu Phe Ser Val Phe Asp Glu Asn Gln Ser Trp Tyr Leu Ala Glu
    575                 580                 585

Asn Ile Gln Arg Phe Leu Pro Asn Pro Asp Gly Leu Gln Pro Gln Asp
590                 595                 600                 605

Pro Glu Phe Gln Ala Ser Asn Ile Met His Ser Ile Asn Gly Tyr Val
            610                 615                 620

Phe Asp Ser Leu Gln Leu Ser Val Cys Leu His Glu Val Ala Tyr Trp
            625                 630                 635

Tyr Ile Leu Ser Val Gly Ala Gln Thr Asp Phe Leu Ser Val Phe Phe
            640                 645                 650

Ser Gly Tyr Thr Phe Lys His Lys Met Val Tyr Glu Asp Thr Leu Thr
    655                 660                 665

Leu Phe Pro Phe Ser Gly Glu Thr Val Phe Met Ser Met Glu Asn Pro
670                 675                 680                 685

Gly Leu Trp Val Leu Gly Cys His Asn Ser Asp Leu Arg Asn Arg Gly
                690                 695                 700

Met Thr Ala Leu Leu Lys Val Tyr Ser Cys Asp Arg Asp Ile Gly Asp
            705                 710                 715

Tyr Tyr Asp Asn Thr Tyr Glu Asp Ile Pro Gly Phe Leu Leu Ser Gly
            720                 725                 730

Lys Asn Val Ile Glu Pro Arg Ser Phe Ala Gln Asn Ser Arg Pro Pro
735                 740                 745

Ser Ala Ser Ala Pro Lys Pro Pro Val Leu Arg Arg His Gln Arg Asp
750                 755                 760                 765

Ile Ser Leu Pro Thr Phe Gln Pro Glu Glu Asp Lys Met Asp Tyr Asp
            770                 775                 780

Asp Ile Phe Ser Thr Glu Thr Lys Gly Glu Asp Phe Asp Ile Tyr Gly
            785                 790                 795
```

```
Glu Asp Glu Asn Gln Asp Pro Arg Ser Phe Gln Lys Arg Thr Arg His
            800                 805                 810
Tyr Phe Ile Ala Ala Val Glu Gln Leu Trp Asp Tyr Gly Met Ser Glu
            815                 820                 825
Ser Pro Arg Ala Leu Arg Asn Arg Ala Gln Asn Gly Glu Val Pro Arg
830                 835                 840                 845
Phe Lys Lys Val Val Phe Arg Glu Phe Ala Asp Gly Ser Phe Thr Gln
                850                 855                 860
Pro Ser Tyr Arg Gly Glu Leu Asn Lys His Leu Gly Leu Leu Gly Pro
                865                 870                 875
Tyr Ile Arg Ala Glu Val Glu Asp Asn Ile Met Val Thr Phe Lys Asn
                880                 885                 890
Gln Ala Ser Arg Pro Tyr Ser Phe Tyr Ser Ser Leu Ile Ser Tyr Pro
        895                 900                 905
Asp Asp Gln Glu Gln Gly Ala Glu Pro Arg His Asn Phe Val Gln Pro
910                 915                 920                 925
Asn Glu Thr Arg Thr Tyr Phe Trp Lys Val Gln His His Met Ala Pro
                930                 935                 940
Thr Glu Asp Glu Phe Asp Cys Lys Ala Trp Ala Tyr Phe Ser Asp Val
                945                 950                 955
Asp Leu Glu Lys Asp Val His Ser Gly Leu Ile Gly Pro Leu Leu Ile
            960                 965                 970
Cys Arg Ala Asn Thr Leu Asn Ala Ala His Gly Arg Gln Val Thr Val
        975                 980                 985
Gln Glu Phe Ala Leu Phe Phe Thr Ile Phe Asp Glu Thr Lys Ser Trp
990                 995                 1000                1005
Tyr Phe Thr Glu Asn Val Glu Arg Asn Cys Arg Ala Pro Cys His
                1010                1015                1020
Leu Gln Met Glu Asp Pro Thr Leu Lys Glu Asn Tyr Arg Phe His
                1025                1030                1035
Ala Ile Asn Gly Tyr Val Met Asp Thr Leu Pro Gly Leu Val Met
                1040                1045                1050
Ala Gln Asn Gln Arg Ile Arg Trp Tyr Leu Leu Ser Met Gly Ser
                1055                1060                1065
Asn Glu Asn Ile His Ser Ile His Phe Ser Gly His Val Phe Ser
                1070                1075                1080
Val Arg Lys Lys Glu Glu Tyr Lys Met Ala Val Tyr Asn Leu Tyr
                1085                1090                1095
Pro Gly Val Phe Glu Thr Val Glu Met Leu Pro Ser Lys Val Gly
                1100                1105                1110
Ile Trp Arg Ile Glu Cys Leu Ile Gly Glu His Leu Gln Ala Gly
                1115                1120                1125
Met Ser Thr Thr Phe Leu Val Tyr Ser Lys Glu Cys Gln Ala Pro
                1130                1135                1140
Leu Gly Met Ala Ser Gly Arg Ile Arg Asp Phe Gln Ile Thr Ala
                1145                1150                1155
Ser Gly Gln Tyr Gly Gln Trp Ala Pro Lys Leu Ala Arg Leu His
                1160                1165                1170
Tyr Ser Gly Ser Ile Asn Ala Trp Ser Thr Lys Asp Pro His Ser
                1175                1180                1185
Trp Ile Lys Val Asp Leu Leu Ala Pro Met Ile Ile His Gly Ile
                1190                1195                1200
Met Thr Gln Gly Ala Arg Gln Lys Phe Ser Ser Leu Tyr Ile Ser
```

-continued

```
                       1205                    1210                    1215
Gln Phe Ile Ile Met  Tyr Ser Leu Asp Gly  Arg Asn Trp Gln Ser
                       1220                    1225                    1230
Tyr Arg Gly Asn Ser  Thr Gly Thr Leu Met  Val Phe Phe Gly Asn
                       1235                    1240                    1245
Val Asp Ala Ser Gly  Ile Lys His Asn Ile  Phe Asn Pro Pro Ile
                       1250                    1255                    1260
Val Ala Arg Tyr Ile  Arg Leu His Pro Thr  His Tyr Ser Ile Arg
                       1265                    1270                    1275
Ser Thr Leu Arg Met  Glu Leu Met Gly Cys  Asp Leu Asn Ser Cys
                       1280                    1285                    1290
Ser Met Pro Leu Gly  Met Gln Asn Lys Ala  Ile Ser Asp Ser Gln
                       1295                    1300                    1305
Ile Thr Ala Ser Ser  His Leu Ser Asn Ile  Phe Ala Thr Trp Ser
                       1310                    1315                    1320
Pro Ser Gln Ala Arg  Leu His Leu Gln Gly  Arg Thr Asn Ala Trp
                       1325                    1330                    1335
Arg Pro Arg Val Ser  Ser Ala Glu Glu Trp  Leu Gln Val Asp Leu
                       1340                    1345                    1350
Gln Lys Thr Val Lys  Val Thr Gly Ile Thr  Thr Gln Gly Val Lys
                       1355                    1360                    1365
Ser Leu Leu Ser Ser  Met Tyr Val Lys Glu  Phe Leu Val Ser Ser
                       1370                    1375                    1380
Ser Gln Asp Gly Arg  Arg Trp Thr Leu Phe  Leu Gln Asp Gly His
                       1385                    1390                    1395
Thr Lys Val Phe Gln  Gly Asn Gln Asp Ser  Ser Thr Pro Val Val
                       1400                    1405                    1410
Asn Ala Leu Asp Pro  Pro Leu Phe Thr Arg  Tyr Leu Arg Ile His
                       1415                    1420                    1425
Pro Thr Ser Trp Ala  Gln His Ile Ala Leu  Arg Leu Glu Val Leu
                       1430                    1435                    1440
Gly Cys Glu Ala Gln  Asp Leu Tyr
                       1445
```